(12) United States Patent
Saunier

(10) Patent No.: US 7,488,356 B2
(45) Date of Patent: *Feb. 10, 2009

(54) COMPOSITION FOR DYEING KERATIN FIBERS, COMPRISING AT LEAST ONE DIAMINO-N,N-DIHYDROPYRAZOLONE DERIVATIVE, AT LEAST ONE COUPLER, AND AT LEAST ONE SURFACTANT

(75) Inventor: Jean-Baptiste Saunier, Paris (FR)

(73) Assignee: L'Oreal S.A., Paris (FR)

( * ) Notice: Subject to any disclaimer, the term of this patent is extended or adjusted under 35 U.S.C. 154(b) by 31 days.

This patent is subject to a terminal disclaimer.

(21) Appl. No.: 11/443,274

(22) Filed: May 31, 2006

(65) Prior Publication Data

US 2006/0277692 A1   Dec. 14, 2006

Related U.S. Application Data

(60) Provisional application No. 60/689,072, filed on Jun. 10, 2005.

(30) Foreign Application Priority Data

May 31, 2005   (FR)   ................... 05 51444

(51) Int. Cl.
  *A61Q 5/10* (2006.01)
  *A01N 43/56* (2006.01)
  *C07D 231/44* (2006.01)

(52) U.S. Cl. ................ 8/405; 8/406; 8/407; 8/408; 8/410; 8/411; 8/412; 8/421; 8/567; 514/406; 514/407; 548/369.1

(58) Field of Classification Search ........ 8/405, 8/406, 407, 408, 410, 411, 412, 421, 567; 514/406, 407; 548/369.1
See application file for complete search history.

(56) References Cited

U.S. PATENT DOCUMENTS

| | | | |
|---|---|---|---|
| 3,649,158 A | 3/1972 | Kalopissis | |
| 4,003,699 A | 1/1977 | Rose et al. | |
| 4,128,425 A | 12/1978 | Greenwald | |
| RE30,199 E | 1/1980 | Rose et al. | |
| 4,314,808 A | 2/1982 | Jacquet et al. | |
| 4,823,985 A | 4/1989 | Grollier et al. | |
| 5,061,289 A | 10/1991 | Clausen et al. | |
| 5,089,025 A | 2/1992 | Rose et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,752,984 A | 5/1998 | Knuebel et al. | |
| 5,766,576 A | 6/1998 | Löwe et al. | |
| 5,865,855 A | 2/1999 | Doehling et al. | |
| 5,931,973 A | 8/1999 | Malle et al. | |
| 6,022,379 A | 2/2000 | Genard et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,391,064 B1 | 5/2002 | Baudry et al. | |
| 6,407,260 B1 | 6/2002 | Bonaventure et al. | |
| 6,432,146 B1 | 8/2002 | Rondeau | |
| 6,464,731 B1 | 10/2002 | Genet et al. | |
| 6,645,258 B2 | 11/2003 | Vidal et al. | |
| 6,692,538 B2 | 2/2004 | Bonaventure et al. | |
| 6,712,861 B2 | 3/2004 | Rondeau | |
| 6,730,789 B1 | 5/2004 | Birault et al. | |
| 6,773,463 B2 | 8/2004 | Pasquier et al. | |
| 6,884,265 B2 | 4/2005 | Vidal et al. | |
| 6,893,471 B2 | 5/2005 | Vidal | |
| 7,001,436 B2 | 2/2006 | Vidal et al. | |
| 7,285,137 B2 * | 10/2007 | Vidal et al. | ................ 8/405 |
| 2001/0023514 A1 | 9/2001 | Cottard et al. | |
| 2003/0124079 A1 | 7/2003 | Mougin et al. | |
| 2003/0172475 A1 * | 9/2003 | Desenne et al. | ............. 8/408 |
| 2004/0060126 A1 | 4/2004 | Cottard et al. | |
| 2004/0141943 A1 | 7/2004 | Mougin et al. | |
| 2004/0194228 A1 | 10/2004 | Lagrange | |
| 2004/0194229 A1 | 10/2004 | Lagrange | |
| 2004/0200009 A1 | 10/2004 | Vidal | |
| 2005/0000037 A1 | 1/2005 | Audousset | |
| 2005/0008594 A1 | 1/2005 | Plos et al. | |
| 2005/0039268 A1 | 2/2005 | Plos et al. | |
| 2005/0060815 A1 | 3/2005 | Kravtchenko et al. | |
| 2005/0076458 A1 | 4/2005 | Cottard et al. | |
| 2005/0166335 A1 | 8/2005 | Vidal et al. | |
| 2005/0183211 A1 | 8/2005 | Samain et al. | |

(Continued)

FOREIGN PATENT DOCUMENTS

DE       16 17 893       6/1971

(Continued)

OTHER PUBLICATIONS

English Language DERWENT Abstract for DE 101 18 271, 2002.

(Continued)

*Primary Examiner*—Eisa B Elhilo
(74) *Attorney, Agent, or Firm*—Finnegan, Henderson, Farabow, Garrett & Dunner LLP

(57) ABSTRACT

Disclosed herein is a composition for dyeing keratin fibers, for example, human keratin fibers such as the hair, comprising at least one oxidation base chosen from diamino-N,N-dihydropyrazolones and the addition salts thereof, at least one coupler, and at least one surfactant chosen from ($C_8$-$C_{30}$)alkyl ether carboxylic acids and salts thereof, ($C_{12}$-$C_{30}$)alkyl polyglucosides, monoglycerolated surfactants, and polyglycerolated surfactants. Also disclosed herein is a method for dyeing keratin fibers comprising applying a composition in accordance with the present disclosure to the keratin fibers. The compositions and methods of the present disclosure may makes it possible to obtain fast coloration of keratin fibers that is resistant to light and/or to washing.

31 Claims, No Drawings

U.S. PATENT DOCUMENTS

2005/0204483 A1    9/2005    Samain et al.
2006/0070191 A1*   4/2006    Lang et al. .................... 8/406

FOREIGN PATENT DOCUMENTS

| | | |
|---|---|---|
| DE | 23 59 399 | 6/1975 |
| DE | 38 25 212 | 2/1990 |
| DE | 38 43 892 | 6/1990 |
| DE | 41 33 957 | 4/1993 |
| DE | 42 34 885 | 4/1994 |
| DE | 44 04 564 | 8/1995 |
| DE | 195 43 988 | 5/1997 |
| DE | 197 30 412 | 12/1998 |
| DE | 101 18 271 | 3/2002 |
| DE | 201 04 441 | 7/2002 |
| DE | 101 48 847 | 4/2003 |
| EP | 0 173 109 | 3/1986 |
| EP | 0 714 954 | 6/1996 |
| EP | 0 770 375 | 5/1997 |
| EP | 0 984 010 | 3/2000 |
| EP | 1 025 834 | 8/2000 |
| EP | 1 166 753 | 1/2002 |
| EP | 1 166 754 | 1/2002 |
| EP | 1 170 000 | 1/2002 |
| EP | 1 170 001 | 1/2002 |
| EP | 1 197 203 | 4/2002 |
| EP | 1 437 123 | 7/2004 |
| EP | 1 464 327 | 10/2004 |
| EP | 1 473 023 | 11/2004 |
| EP | 1 550 656 | 7/2005 |
| EP | 1 598 047 | 11/2005 |
| FR | 1 584 111 | 12/1969 |
| FR | 2 456 764 | 12/1980 |
| FR | 2 586 913 | 3/1987 |
| FR | 2 733 749 | 11/1996 |
| FR | 2 746 392 | 9/1997 |
| FR | 2 750 048 | 12/1997 |
| FR | 2 760 010 | 8/1998 |
| FR | 2 782 452 | 2/2000 |
| FR | 2 788 273 | 7/2000 |
| FR | 2 798 931 | 3/2001 |
| FR | 2 801 308 | 5/2001 |
| FR | 2 803 195 | 7/2001 |
| FR | 2 811 993 | 1/2002 |
| FR | 2 817 467 | 6/2002 |
| FR | 2 822 696 | 10/2002 |
| FR | 2 825 622 | 12/2002 |
| FR | 2 825 625 | 12/2002 |
| FR | 2 825 702 | 12/2002 |
| FR | 2 825 703 | 12/2002 |
| FR | 2 833 834 | 6/2003 |
| FR | 2 845 387 | 4/2004 |
| FR | 2 848 837 | 6/2004 |
| FR | 2 848 840 | 6/2004 |
| FR | 2 855 966 | 12/2004 |
| FR | 2 855 967 | 12/2004 |
| GB | 1 026 978 | 4/1966 |
| GB | 1 153 196 | 5/1969 |
| GB | 1 213 697 | 11/1970 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 00/10519 * | 3/2000 |
| WO | WO 02/22093 | 3/2002 |

OTHER PUBLICATIONS

English Language DERWENT Abstract for DE 101 48 847, 2003.
English Language DERWENT Abstract for DE 201 04 441, 2002.
English Language DERWENT Abstract for EP 0 770 375, 1997.
English Language DERWENT Abstract for EP 1 197 203, 2002.
English Language DERWENT Abstract for FR 2 456 764, 1980.
English Language DERWENT Abstract for JP 2-19576, 1990.
English Language DERWENT Abstract for JP 5-163124, 1993.
Co-pending U.S. Appl. No. 11/443,273, Title: Composition for Dyeing Keratin Fibers, Comprising a Diamino-N,N-Dihydropyrazolone Derivative, a Coupler and a Polyol Inventors: Jean-Baptiste Saunier filed May 31, 2006.
Co-pending U.S. Appl. No. 11/443,353, Title: Composition for Dyeing Keratin Fibers, Comprising at Least One Diamino-N,N-Dihydropyrazolone Derivative, at Least One Coupler and at Least One Associative Polyurethane Polymer Inventors: Jean-Baptiste Saunier filed May 31, 2006.
Co-pending U.S. Appl. No. 11/442,967, Title: Composition for Dyeing Keratin Fibers, Comprising at Least One Diamino-N,N-Dihydropyrazolone Derivative, at Least One Coupler, and at Least One Heterocyclic Direct Dye Inventors: Leila Hercouet filed May 31, 2006.
European Search Report for EP 06 11 4654, mailed Aug. 23, 2006 (corresponding to U.S. Appl. No. 11/443,273).
European Search Report for EP 06 11 4652, mailed Aug. 23, 2006 (corresponding to the present application).
European Search Report for EP 06 11 4656, mailed Sep. 22, 2006 (corresponding to U.S. Appl. No. 11/443,353).
European Search Report for EP 06 11 4655, mailed Sep. 22, 2006 (corresponding to U.S. Appl. No. 11/442,967).
French Report for FR 05 51445, mailed Feb. 6, 2006 (corresponding to U.S. Appl. No. 11/443,273).
French Report for FR 05 51444, mailed Feb. 6, 2006 (corresponding to the present application).
French Report for FR 05 51429, mailed Feb. 1, 2006 (corresponding to U.S. Appl. No. 11/443,353).
French Report for FR 05 51446, mailed Feb. 1, 2006 (corresponding to U.S. Appl. No. 11/442,967).
Boros et al., *J. Het. Chem.*, 38(3): 613-616 (2001).
Cohen & Zand, *J. Am. Chem. Soc.*, 84: 586-590 (1962).
Fonnum et al., *Colloid Polym. Sci*, 271(4): 380-389 (1993).
Heyman & Snyder, *Tetrahedron. Letters*, 30: 2859-2862 (1973).
Kharasch & Bruice, *J. Am. Chem. Soc.*, 73: 3240-3244 (1951).
Lingens and Shneider-Bernlöhr, *Justus Liebig Ann. Chem.*, 686: 134-144 (1965).
Magnien & Baltzly, *J. Org. Chem.*, 23: 2029-2032 (1958).
Stenzl et al., *Helvetica Chimica Acta*, 33: 1183-1194 (1950).

* cited by examiner

COMPOSITION FOR DYEING KERATIN FIBERS, COMPRISING AT LEAST ONE DIAMINO-N,N-DIHYDROPYRAZOLONE DERIVATIVE, AT LEAST ONE COUPLER, AND AT LEAST ONE SURFACTANT

This application claims benefit of U.S. Provisional Application No. 60/689,072, filed Jun. 10, 2005, the contents of which are incorporated herein by reference. This application also claims benefit of priority under 35 U.S.C. § 119 to French Patent Application No. FR 05 51444, filed May 31, 2005, the contents of which are also incorporated herein by reference.

Disclosed herein is a composition for dyeing keratin fibers, for example, human keratin fibers such as the hair, comprising at least one oxidation base chosen from diamino-N,N-dihydropyrazolones and the addition salts thereof, at least one coupler, and at least one surfactant chosen from ($C_8$-$C_{30}$)alkyl ether carboxylic acids and salts thereof, ($C_{12}$-$C_{30}$)alkyl polyglucosides, monoglycerolated surfactants, and polyglycerolated surfactants. Also disclosed herein is a method for dyeing keratin fibers, comprising applying such a composition to the keratin fibers.

It is common practice to dye keratin fibers, for example, human keratin fibers such as the hair, with dye compositions comprising oxidation dye precursors, for instance, ortho- or para-phenylenediamines, ortho- or para-aminophenols, and heterocyclic compounds such as diaminopyrazole derivatives, pyrazolo[1,5-a]-pyrimidine derivatives, pyrimidine derivatives, pyridine derivatives, indole derivatives, and indoline derivatives, which are generally known as oxidation bases. Oxidation dye precursors, or oxidation bases, are colorless or weakly colored compounds that, when combined with oxidizing products, can give rise to colored compounds and dyes via a process of oxidative condensation. Permanent colorations may thus be obtained.

It is also known that the shades obtained with these oxidation bases may be varied by combining them with couplers and/or coloration modifiers, the latter being chosen, for example, from meta-phenylenediamines, meta-aminophenols, meta-hydroxyphenols, and hetero-cyclic compounds.

The variety of molecules available for use as oxidation bases and couplers may allow a wide range of colors to be obtained.

The use of oxidation bases such as para-phenylene-diamine and para-aminophenol derivatives may allow a broad range of colors to be obtained at basic pH without, however, achieving shades with good chromaticity, while at the same time giving the hair excellent properties such as strength of color, variety of shades, uniformity of the color, and/or fastness with respect to external agents.

The use of these bases at neutral pH may not allow a varied range of shades to be produced, for example, warm shades such as reds and oranges.

Thus, the present disclosure provides compositions for dyeing keratin fibers that may make it possible to obtain a strong, chromatic, aesthetic, and/or sparingly selective coloration in varied shades, which may also show good resistance to the various attacking factors to which the hair may be subjected, such as shampoo, light, sweat, and/or permanent reshaping operations.

Disclosed herein is a composition for dyeing keratin fibers, comprising, in a suitable, i.e., cosmetically acceptable, medium:

(a) at least one oxidation base chosen from diamino-N,N-dihydropyrazolone derivatives of formula (I) and addition salts thereof:

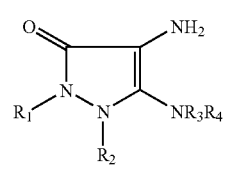

wherein:
  $R_1$, $R_2$, $R_3$, and $R_4$, which may be identical or different, are chosen from:
    linear or branched $C_1$-$C_{10}$, for example, $C_1$-$C_6$, alkyl radicals optionally substituted with at least one radical chosen from $OR_5$ radicals, $NR_6R_7$ radicals, carboxyl radicals, sulfonic radicals, carboxamido radicals $CONR_6R_7$, sulfonamido radicals $SO_2NR_6R_7$, and heteroaryl and aryl radicals optionally substituted with at least one group chosen from ($C_1$-$C_4$)alkyl, hydroxyl, $C_1$-$C_2$ alkoxy, amino, and (di)($C_1$-$C_2$)alkylamino groups;
    aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals; and
    5- or 6-membered heteroaryl radicals, optionally substituted with at least one radical chosen from ($C_1$-$C_4$) alkyl and ($C_1$-$C_2$)alkoxy radicals;
  $R_3$ and $R_4$ may also be hydrogen;
  $R_5$, $R_6$, and $R_7$, which may be identical or different, are chosen from:
    hydrogen;
    linear or branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$, and aryl radicals optionally substituted with at least one radical chosen from ($C_1$-$C_4$) alkyl, hydroxyl, $C_1$-$C_2$ alkoxy, amino, and (di)($C_1$-$C_2$)alkylamino radicals; and aryl radicals optionally substituted with at least one radical chosen from ($C_1$-$C_4$)alkyl, hydroxyl, $C_1$-$C_2$ alkoxy, amino, and (di) ($C_1$-$C_2$)alkylamino radicals;
  $R_6$ and $R_7$, which may be identical or different, may also be chosen from carboxamido radicals $CONR_8R_9$ and sulfonyl radicals $SO_2R_8$;
  $R_8$ and $R_9$, which may be identical or different, may be chosen from hydrogen and linear or branched $C_1$-$C_4$ alkyl radicals optionally substituted with at least one radical chosen from hydroxyl and $C_1$-$C_2$ alkoxy radicals;
  $R_1$ and $R_2$, and $R_3$ and $R_4$, may form, together with the nitrogen atoms to which they are attached, a saturated or unsaturated 5- to 7-membered heterocycle optionally substituted with at least one entity chosen from halogen atoms, amino radicals, (di)($C_1$-$C_4$)alkylamino radicals, hydroxyl radicals, carboxyl radicals, carboxamido radicals, ($C_1$-$C_2$)alkoxy radicals, and $C_1$-$C_4$ alkyl radicals optionally substituted with at least one radical chosen from hydroxyl, amino, (di)alkylamino, alkoxy, carboxyl, and sulfonyl radicals; and
  $R_3$ and $R_4$ may also form, together with the nitrogen atom to which they are attached, a 5- or 7-membered heterocycle, the carbon atoms of which may be replaced with an entity chosen from oxygen and optionally substituted nitrogen;

(b) at least one coupler; and
(c) at least one surfactant chosen from $(C_8-C_{30})$alkyl ether carboxylic acids and salts thereof, $(C_{12}-C_{30})$alkyl polyglucosides, monoglycerolated surfactants, and polyglycerolated surfactants.

The compositions of the present disclosure may make it possible to obtain a strong, aesthetic, and/or sparingly selective coloration of keratin fibers in varied shades, which may also show good resistance to the various attacking factors to which the hair may be subjected, such as shampoo, light, sweat, and/or permanent reshaping operations. These compositions may furthermore make it possible to obtain intense and varied colorations at neutral pH.

Also disclosed herein is a method for dyeing keratin fibers comprising applying a composition of the present disclosure to the keratin fibers.

Further disclosed herein is a dyeing kit comprising a dye composition comprising at least one oxidation base of formula (I), at least one coupler, and at least one surfactant chosen from $(C_8-C_{30})$alkyl ether carboxylic acids and salts thereof, $(C_{12}-C_{30})$alkyl polyglucosides, monoglycerolated surfactants, and polyglycerolated surfactants, and a composition comprising at least one oxidizing agent.

As used herein, the term "alkyl radical" refers to linear or branched alkyl radicals which are $C_1-C_{10}$ unless otherwise indicated, for example, $C_1-C_6$, or $C_1-C_4$, such as methyl, ethyl, propyl, isopropyl, isobutyl, tert-butyl, pentyl, and hexyl radicals.

Hereinafter, the expression "ranging from x to y" means in the range from x to y, the limits x and y being included.

Oxidation Bases

In at least one embodiment, in formula (I), the radicals $R_1$ and $R_2$, which may be identical or different, may be chosen from:

$C_1-C_6$ alkyl radicals optionally substituted with at least one radical chosen from hydroxyl, $(C_1-C_2)$alkoxy, amino, and (di)$(C_1-C_2)$alkylamino radicals; and phenyl, methoxyphenyl, ethoxyphenyl, and benzyl radicals.

In another embodiment, the radicals $R_1$ and $R_2$, which may be identical or different, may be chosen from methyl, ethyl, 2-hydroxyethyl, 3-hydroxypropyl, 2-hydroxypropyl, and phenyl radicals.

According to yet another embodiment, the radicals $R_1$ and $R_2$ may form, together with the nitrogen atoms to which they are attached, a saturated or unsaturated, optionally substituted 5- or 6-membered ring.

In a further embodiment, the radicals $R_1$ and $R_2$ may form, together with the nitrogen atoms to which they are attached, a ring chosen from pyrazolidine and pyridazolidine rings, optionally substituted with at least one radical chosen from $C_1-C_4$ alkyl, hydroxyl, $(C_1-C_2)$alkoxy, carboxyl, carboxamido, amino, and (di)$(C_1-C_2)$alkylamino radicals.

In still a further embodiment, the radicals $R_1$ and $R_2$ may form, together with the nitrogen atoms to which they are attached, a ring chosen from pyrazolidine and pyridazolidine rings.

The radicals $R_3$ and $R_4$, which may be identical or different, may, in at least one embodiment, be chosen from hydrogen; linear or branched $C_1-C_6$ alkyl radicals optionally substituted with at least one radical chosen from hydroxyl, $(C_1-C_2)$ alkoxy, amino, and (di)$(C_1-C_2)$alkylamino radicals; and phenyl radicals optionally substituted with at least one radical chosen from hydroxyl, amino, and $(C_1-C_2)$alkoxy radicals.

In another embodiment, the radicals $R_3$ and $R_4$, which may be identical or different, may be chosen from hydrogen, methyl, ethyl, isopropyl, 2-hydroxyethyl, 3-hydroxypropyl, 2-hydroxypropyl, and 2-carboxyethyl radicals. According to yet another embodiment, the radicals $R_3$ and $R_4$ may be hydrogen.

According to still another embodiment, the radicals $R_3$ and $R_4$ may form, together with the nitrogen atom to which they are attached, a 5- or 7-membered ring chosen from pyrrolidine, piperidine, homopiperidine, piperazine, and homopiperazine heterocycles; said rings optionally being substituted with at least one radical chosen from hydroxyl, amino, (di)$(C_1-C_2)$alkylamino, carboxyl, carboxamido, and $C_1-C_4$ alkyl radicals optionally substituted with at least one radical chosen from hydroxyl, amino, and $C_1-C_2$ (di)alkylamino radicals.

In a further embodiment, the radicals $R_3$ and $R_4$ may form, together with the nitrogen atom to which they are attached, a 5- or 7-membered ring chosen from pyrrolidine, 2,5-di-methylpyrrolidine, pyrrolidine-2-carboxylic acid, 3-hydroxy-pyrrolidine-2-carboxylic acid, 4-hydroxy-pyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethyl-pyrrolidine, 3,4-dihydroxy-2-hydroxymethylpyrrolidine, 3-hydroxypyrrolidine, 3,4-dihydroxypyrrolidine, 3-amino-pyrrolidine, 3-methylaminopyrrolidine, 3-dimethylamino-pyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethyl piperidine, 3-hydroxy-2-hydroxymethylpiperidine, 3-hydroxy-piperidine, 4-hydroxypiperidine, 3-hydroxymethyl-piperidine, homopiperidine, 2-carboxyhomopiperidine, 2-carboxamidohomopiperidine, homopiperazine, N-methyl-homopiperazine, and N-(2-hydroxyethyl)homopiperazine.

According to another embodiment, the radicals $R_3$ and $R_4$ may form, together with the nitrogen atom to which they are attached, a 5- or 7-membered ring chosen from pyrrolidine, 3-hydroxy-pyrrolidine, 3-aminopyrrolidine, 3-dimethylamino-pyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-β-hydroxyethyl-homopiperazine.

In accordance with yet another embodiment of the present disclosure, the radicals $R_3$ and $R_4$ may form, together with the nitrogen atom to which they are attached, a 5-membered ring such as pyrrolidine, 3-hydroxy-pyrrolidine, 3-aminopyrrolidine, and 3-dimethylamino-pyrrolidine.

The compounds of formula (I) may be optionally salified with at least one acid chosen from strong mineral acids, for instance, HCl, HBr, HI, $H_2SO_4$, and $H_3PO_4$; and organic acids, for instance, acetic acid, lactic acid, tartaric acid, citric acid, succinic acid, benzenesulfonic acid, para-toluenesulfonic acid, formic acid, and methanesulfonic acid.

The compounds of formula (I) may also be in the form of solvates, for example, hydrates and solvates of linear or branched alcohols such as ethanol and isopropanol.

Examples of derivatives of formula (I) include, but are not limited to:

4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one;
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;

4-amino-5-(piperid-1-yl)-1,2-dimethyl-1,2-dihydropyrazol-3-one;
4,5-diamino-1,2-di(2-hydroxyethyl)-1,2-dihydropyrazol-3-one;
4-amino-5-methylamino-1,2-di(2-hydroxyethyl)-1,2-dihydropyrazol-3-one;
4-amino-5-dimethylamino-1,2-di(2-hydroxyethyl)-1,2-dihydropyrazol-3-one;
4-amino-5-(2-hydroxyethyl)amino-1,2-di(2-hydroxyethyl)-1,2-dihydropyrazol-3-one;
4-amino-5-(pyrrolidin-1-yl)-1,2-di(2-hydroxyethyl)-1,2-dihydropyrazol-3-one;
4-amino-5-(piperid-1-yl)-1,2-di(2-hydroxyethyl)-1,2-dihydropyrazol-3-one;
4,5-diamino-1,2-diethyl-1,2-dihydropyrazol-3-one;
4,5-diamino-1,2-phenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperid-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-1,2-diethyl-5-(3-hydroxypyrrolidin-1-yl)-1,2-dihydropyrazol-3-one;
4-amino-1,2-diethyl-5-pyrrolidin-1-yl-1,2-dihydro-pyrazol-3-one;
4-amino-5-(3-dimethylaminopyrrolidin-1-yl)-1,2-diethyl-1,2-dihydropyrazol-3-one;
4-amino-1,2-diethyl-5-(4-methylpiperazin-1-yl)-pyrazolidin-3-one;
2,3-diamino-6-hydroxy-6,7-dihydro-5H-pyrazolo[1,2-a]pyrazol-1-one; and the addition salts thereof, some of which are depicted below to illustrate the names with the corresponding chemical structures:

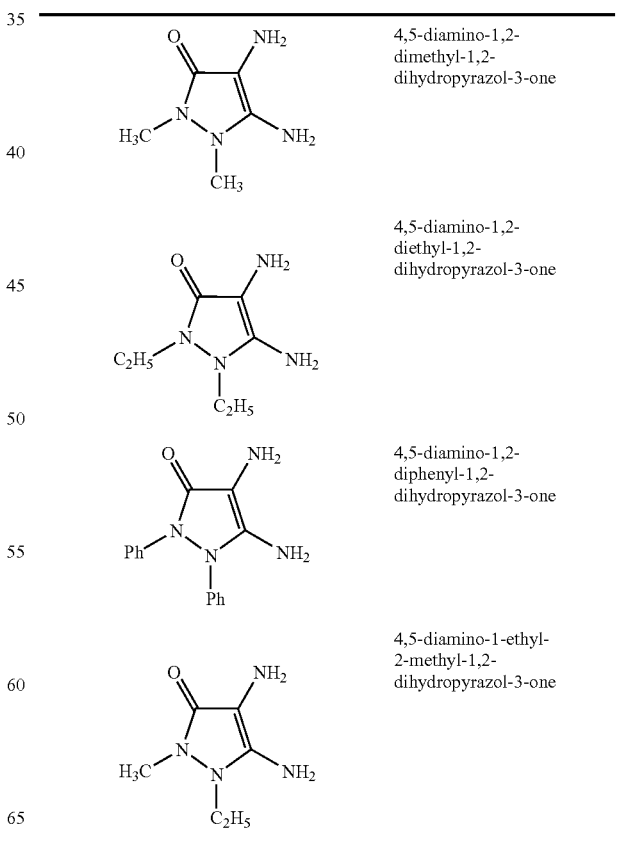

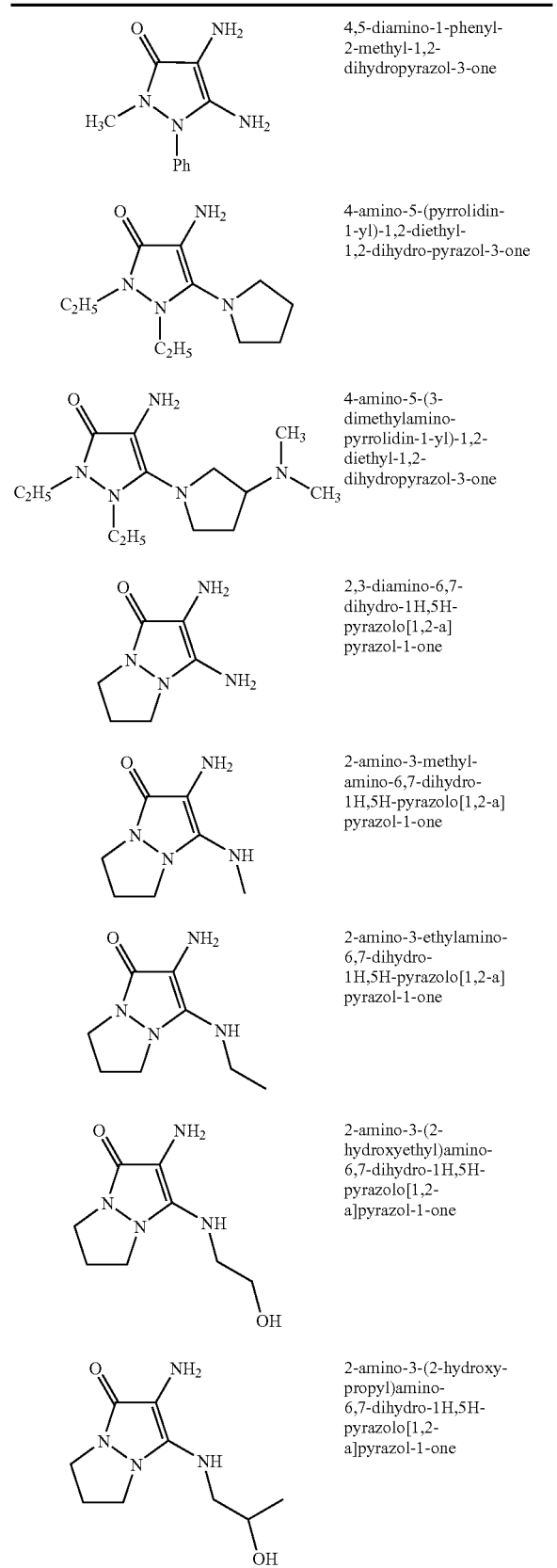
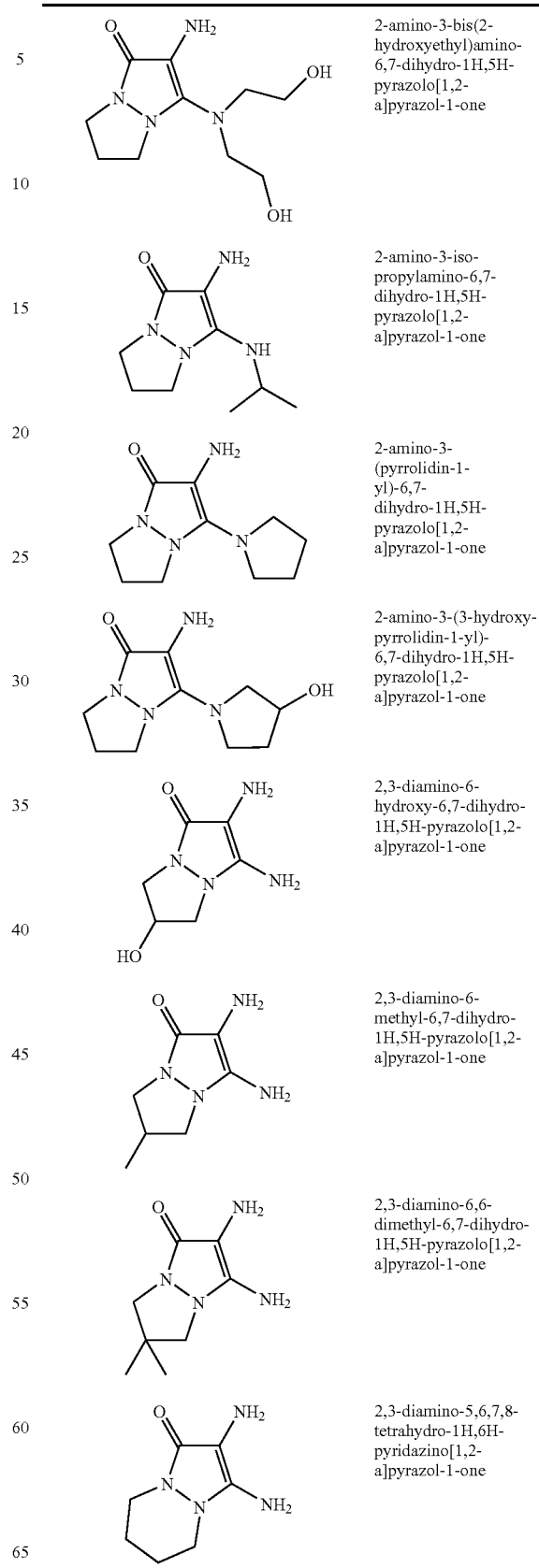

| | |
|---|---|
| 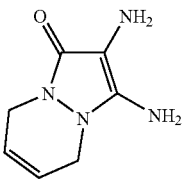 | 2,3-diamino-5,8-dihydro-1H,6H-pyridazino[1,2-a]pyrazol-1-one |
| 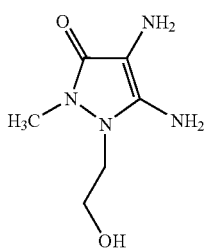 | 4,5-diamino-1-(2-hydroxyethyl)-2-methyl-1,2-dihydropyrazol-3-one |
| 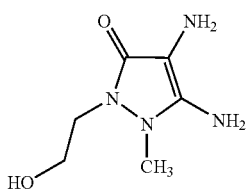 | 4,5-diamino-2-(2-hydroxyethyl)-1-methyl-1,2-dihydropyrazol-3-one |

In one embodiment, the diamino-N,N-dihydro-pyrazolone derivatives of formula (I), or the addition salts thereof, may be chosen from:

2,3-diamino-6,7-dihydro-1H,5H-pyrazolo[1,2-a]pyrazol-1-one;

2-amino-3-ethylamino-6,7-dihydro-1H,5H-pyrazolo[1,2-a]pyrazol-1-one;

2-amino-3-isopropylamino-6,7-dihydro-1H,5H-pyrazolo[1,2-a]pyrazol-1-one;

2-amino-3-(pyrrolidin-1-yl)-6,7-dihydro-1H,5H-pyrazolo[1,2-a]pyrazol-1-one;

4,5-diamino-1,2-dimethyl-1,2-dihydropyrazol-3-one;

4,5-diamino-1,2-diethyl-1,2-dihydropyrazol-3-one;

4,5-diamino-1,2-di(2-hydroxyethyl)-1,2-dihydropyrazol-3-one;

2-amino-3-(2-hydroxyethyl)amino-6,7-dihydro-1H,5H-pyrazolo[1,2-a]pyrazol-1-one;

2-amino-3-dimethylamino-6,7-dihydro-1H,5H-pyrazolo[1,2-a]pyrazol-1-one;

2,3-diamino-5,6,7,8-tetrahydro-1H,6H-pyridazino[1,2-a]pyrazol-1-one;

4-amino-1,2-diethyl-5-pyrrolidin-1-yl-1,2-dihydropyrazol-3-one;

4-amino-5-(3-dimethylaminopyrrolidin-1-yl)-1,2-diethyl-1,2-dihydropyrazol-3-one; and 2,3-diamino-6-hydroxy-6,7-dihydro-1H,5H-pyrazolo[1,2-a]pyrazol-1-one.

The at least one oxidation base of formula (I) may be present in the dye composition in an amount ranging from 0.001% to 10% by weight, for example, ranging from 0.005% to 6% by weight, relative to the total weight of the dye composition.

Couplers

The at least one coupler may be chosen, for example, from meta-phenylenediamines, meta-aminophenols, meta-diphenols, naphthalene-based couplers, heterocyclic couplers, and the addition salts thereof.

Non-limiting examples of suitable couplers include 2-methyl-5-aminophenol, 5-N-(β-hydroxyethyl)amino-2-methylphenol, 6-chloro-2-methyl-5-aminophenol, 3-aminophenol, 1,3-di-hydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxy-benzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxy-benzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

The at least one coupler may be present in the dye composition in an amount ranging from 0.001% to 10% by weight, for example, from 0.005% to 6% by weight, relative to the total weight of the dye composition.

Surfactants

Alkyl Ether Carboxylic Acids

The at least one surfactant may be chosen from alkyl ether carboxylic acids and salts thereof, for example, those of formula (II) below:

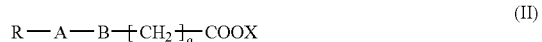

wherein:

R is chosen from linear or branched $C_{8-22}$ alkyl and alkylene radicals and $(C_8-C_9)$alkylaryl radicals such as $(C_8-C_9)$alkylphenyl radicals;

A is chosen from oxygen, —CO—, —NH—, and —CO—O—;

B is chosen from random sequences and blocks of p units —$C_3H_6O$— and n units —$C_2H_4O$—;

n is an integer ranging from 1 to 30;

p is an integer ranging from 0 to 15;

q is an integer equal to 0 or 1; and

X is chosen from hydrogen, Na, K, Li, ½ Mg, monoethanolamine residues, ammonium residues, and triethanolamine residues.

According to one embodiment of the present disclosure, the alkyl ether carboxylic acids and salts thereof may be chosen from those of formula (II) in which R is chosen from $C_8-C_{22}$, for instance, $C_{10}-C_{18}$, alkyl radicals, A is oxygen, X is chosen from hydrogen and sodium, p is equal to 0, n is an integer ranging from 1 to 20, for instance, from 1 to 10, and q is equal to 0 or 1.

The commercial products corresponding to compounds of formula (II) may comprise a mixture of alkyl ether carboxylic acids and/or salts thereof, and in this case it is the mean of the values of n and/or p that are indicated. While n and p are integers in formula (II) above, the mean values for commercial products may be reported as decimal values, for example, as tenths. Examples of suitable commercial products include the products sold by the company Chem Y under the names:

Akypo® NP 70 (R=nonylphenyl, A=O, n=7, p=0, q=1, X=H);

Akypo® NP 40 (R=nonylphenyl, A=O, n=4, p=0, q=1, X=H);

Akypo® OP 40 (R=octylphenyl, A=O, n=4, p=0, q=1, X=H);

Akypo® OP 80 (R=octylphenyl, A=O, n=8, p=0, q=1, X=H);

Akypo® OP 190 (R=octylphenyl, A=O, n=19, p=0, q=1, X=H);

Akypo® RLM 38 (R=($C_{12}$-$C_{14}$)alkyl, A=O, n mean=3.8, p=0, q=1, X=H);
Akypo® RLM 38 NV (R=($C_{12}$-$C_{14}$)alkyl, A=O, n=4, p=0, q=1, X=Na);
Akypo® RLM 45 (R=($C_{12}$-$C_{14}$)alkyl, A=O, n mean=4.5, p=0, q=1, X=H);
Akypo® RLM 45 NV (R=($C_{12}$-$C_{14}$)alkyl, A=O, n mean=4.5, p=0, q=1, X=Na);
Akypo® RLM 100 (R=($C_{12}$-$C_{14}$)alkyl, A=O, n=10, p=0, q=1, X=H);
Akypo® RLM 100 NV (R=($C_{12}$-$C_{14}$)alkyl, A=O, n=10, p=0, q=1, X=Na);
Akypo® RLM 130 (R=($C_{12}$-$C_{14}$)alkyl, A=O, n=13, p=0, q=1, X=Na);
Akypo® RLM 160 NV (R=($C_{12}$-$C_{14}$)alkyl, A=O, n=16, p=0, q=1, X=Na);
Akypo® RS 60 (R=($C_{17}$)alkyl, A=—CO—O—, n=6, p=0, q=1, X=H);
Akypo® RCS 60 (R=cetyl, A=0/R=($C_{17}$)alkyl, A=—CO—O—; n=6, p=0, q=1, X=H);
Akypo® RS 100 (R-A=stearyl, n=10, p=0, q=1, X=H);
Akypo® RO 50 (R-A=oleyl, n=5, p=0, q=1, X=H);
Akypo® Soft 70 NV;
Akypo® Soft 45 NV;
Akypo® Soft 100 NV;
Akypo® RLM 45 CA;
Akypo® RLM 70;
Akypo® TFC;
Akypo® FOM 30 (R=lauryl, A=NH); and
Akypo® Surfine WLL;

and those sold by the company Sandoz under the names:
Sandopan ACA-48 (R=cetyl, A=O/($C_{17}$)alkyl, A=—CO—O—; n=24, p=0, q=1, X=H);
Sandopan DTC-Acid (R=alkyl, A=O, n=6, p=0, q=1, X=H);
Sandopan DTC (R=($C_{13}$)alkyl, A=O, n=6, p=0, q=1, X=Na);
Sandopan LS 24 (R=($C_{12}$-$C_{14}$)alkyl, A=O, n=12, p=0, q=1, X=Na); and
Sandopan JA 36 (R=($C_{13}$)alkyl, A=O, n=18, p=0, q=1, X=H).

Alkyl Polyglucosides

The at least one surfactant may also be chosen from alkyl polyglucosides, such as those of formula (III):

wherein:
  $R'_1$ is chosen from linear or branched alkyl and/or alkylene radicals comprising from 12 to 30 carbon atoms, and alkylphenyl radicals in which the linear or branched alkyl radical comprises from 12 to 30 carbon atoms,
  $R'_2$ is chosen from alkylene radicals comprising from 2 to 4 carbon atoms,
  G is a sugar unit comprising from 5 to 6 carbon atoms,
  t is a number ranging from 0 to 10, for example, from 0 to 4, and
  v is a number ranging from 1 to 15.

According to one embodiment of the present disclosure, the alkyl polyglucosides may be chosen from compounds of formula (III), in which $R'_1$ is chosen from linear or branched, saturated or unsaturated alkyl radicals comprising from 12 to 30 carbon atoms, t is a number ranging from 0 to 3, and in at least one embodiment, is equal to 0, and G is chosen from glucose, fructose, and galactose, and in at least one embodiment, glucose. The degree of polymerization, i.e., the value of v in formula (III), may range from 1 to 15, for example, from 1 to 4. The mean degree of polymerization may range from 1 to 2, for example, from 1.1 to 1.5.

The glycoside bonds between the sugar units may be chosen from 1-6 and 1-4 bonds, and in at least one embodiment, are 1-4 bonds.

Examples of commercial products corresponding to compounds of formula (III) include, but are not limited to, products sold by the company Cognis under the names Plantaren® (600 CS/U, 1200, and 1300) and Plantacare® (818 and 1200).

The at least one surfactant may be chosen from monoglycerolated and polyglycerolated surfactants, for example, those comprising on average from 1 to 30 glycerol groups, for instance, from 1 to 10, or from 1.5 to 5 glycerol groups.

The monoglycerolated and polyglycerolated surfactants may be chosen from compounds of the following formulae:

in which R' is chosen from linear or branched, saturated or unsaturated hydrocarbon-based radicals comprising from 8 to 40 carbon atoms, for example, from 10 to 30 carbon atoms; m is a number ranging from 1 to 30, for example, from 1 to 10, or from 1.5 to 6.

R' may optionally comprise at least one heteroatom, for instance, oxygen and nitrogen. In one embodiment, R' may optionally comprise at least one hydroxyl, ether, and/or amide group.

In another embodiment, R' may be chosen from optionally monohydroxylated and polyhydroxylated $C_{10}$-$C_{20}$ alkyl radicals and optionally monohydroxylated and polyhydroxylated $C_{10}$-$C_{20}$ alkylene radicals.

The polyglycerolated (3.5 mol) hydroxylauryl ether sold under the name Chimexane® NF from Chimex is suitable for use as a polyglycerolated surfactant.

In one embodiment, the at least one surfactant may be chosen from lauryl ether carboxylic acid, (68/26/6 $C_{12}$/$C_{14}$/$C_{16}$)alkyl polyglucoside, and cetearyl alcohol polyglycerolated with r moles of glycerol, r being an integer ranging from 2 to 10, for example, from 2 to 6.

The at least one surfactant may be present in the dye composition in an amount ranging from 0.01% to 30% by weight, for example, from 0.1% to 15% by weight, relative to the total weight of the dye composition.

The dye composition of the present disclosure may optionally comprise at least one additional oxidation base other than those of formula (I), which may be chosen from those conventionally used for the dyeing of keratin fibers.

The composition of the present disclosure may comprise, for example, at least one additional oxidation base chosen from para-phenylenediamines, bis(phenyl)alkylenediamines, para-aminophenols, bis-para-aminophenols, ortho-aminophenols, ortho-phenylenediamines and heterocyclic bases other than the derivatives of formula (I) as defined above, and the addition salts thereof.

Examples of para-phenylenediamines include, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylamino-ethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the acid addition salts thereof.

In one embodiment, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Non-limiting examples of suitable bis(phenyl)alkylenediamines include N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Suitable para-aminophenols include, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Examples of ortho-aminophenols include, for example, 2-aminophenol, 2-amino-5-methylphenol, 2-amino-6-methylphenol, 5-acetamido-2-aminophenol, and the acid addition salts thereof.

The heterocyclic bases may be chosen, for example, from pyridine derivatives, pyrimidine derivatives, and pyrazole derivatives.

Non-limiting examples of pyridine derivatives include the compounds described, for example, in British Patent Nos. 1 026 978 and 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

Other pyridine oxidation bases suitable for use in the present disclosure include 3-aminopyrazolo[1,5-a]pyridine oxidation bases and the addition salts thereof described, for example, in French Patent Application No. 2 801 308, for example, pyrazolo[1,5-a]pyrid-3-ylamine; 2-acetylaminopyrazolo[1,5-a]pyrid-3-ylamine; 2-morpholin-4-yl pyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-yl-pyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxy-ethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and the acid and base addition salts thereof.

Suitable pyrimidine derivatives may be chosen, for instance, from the compounds described, for example, in German Patent No. 2 359 399; Japanese Patent Application No. 88-169 571; Japanese Patent No. 05 63 124; European Patent No. 0 770 375, and International Patent Application Publication No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, and 2,5,6-triaminopyrimidine, and pyrazolopyrimidine derivatives such as those mentioned in French Patent Application No. 2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, the acid addition salts thereof, and the tautomeric forms thereof, when a tautomeric equilibrium exists.

Examples of suitable pyrazole derivatives include, for example, the compounds described in German Patent Nos. 195 43 988, 3 843 892, and 4 133 957, International Patent Application Publication Nos. WO 94/08969 and WO 94/08970, and French Patent No. 2 733 749, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

The at least one optional additional oxidation base may be present in the dye composition in an amount ranging from 0.001% to 10% by weight relative to the total weight of the dye composition, for example, from 0.005% to 6%.

In general, the addition salts of the oxidation bases and of the couplers that may be used in the present disclosure may be chosen from acid addition salts, such as hydrochlorides, hydrobromides, sulfates, citrates, succinates, tartrates, lactates, tosylates, benzenesulfonates, phosphates, and acetates, and base addition salts, such as sodium hydroxide, potassium hydroxide, ammonia, amines, and alkanolamines.

The dye composition may also comprise at least one direct dye, which may be chosen from nitrobenzene dyes, azo direct dyes, and methine direct dyes. In one embodiment, the direct dyes may be chosen from nonionic, anionic, and cationic direct dyes.

The medium suitable for dyeing, also known as the dye support, is a cosmetic medium chosen, for example, from water and mixtures of water and at least one organic solvent to dissolve the compounds which would not be sufficiently soluble in water. Examples of suitable organic solvents, include, for example, $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether, and monomethyl ether; aromatic alcohols such as benzyl alcohol and phenoxyethanol; and mixtures thereof.

The at least one organic solvent may be present in the dye composition in an amount ranging from 1% to 40% by weight relative to the total weight of the dye composition, for example, from 5% to 30% by weight.

The dye composition in accordance with the present disclosure may also comprise at least one adjuvant conventionally used in compositions for dyeing the hair, such as anionic, cationic, nonionic, amphoteric, or zwitterionic surfactants other than the surfactants described herein, and mixtures thereof; anionic, cationic, nonionic, amphoteric, or zwitterionic polymers and mixtures thereof; inorganic or organic thickeners, for example, anionic, cationic, nonionic, or amphoteric associative polymeric thickeners; antioxidants; penetrants; sequestrants; fragrances; buffers; dispersants; conditioning agents, for instance, silicones, which may be volatile or non-volatile, and modified or unmodified; film-forming agents; ceramides; preserving agents; and opacifiers.

The at least one adjuvant may be present in the dye composition in an amount ranging from 0.01% to 20% by weight relative to the total weight of the dye composition.

It is to be understood that a person skilled in the art will take care to select this or these optional additional compounds such that the advantageous properties intrinsically associated with the oxidation dye composition in accordance with the present disclosure are not, or are not substantially, adversely affected by the addition envisaged.

The pH of the dye composition in accordance with the present disclosure may range from 3 to 12, for example, from 5 to 11. The pH may be adjusted to the desired value using acidifying or basifying agents conventionally used in the dyeing of keratin fibers, or by using standard buffer systems.

Examples of acidifying agents may include, for example, inorganic and organic acids such as hydrochloric acid; orthophosphoric acid; sulfuric acid; carboxylic acids such as acetic acid, tartaric acid, citric acid, and lactic acid; and sulfonic acids.

Suitable basifying agents include, for example, aqueous ammonia, alkaline carbonates, alkanolamines such as mono-, di-, and triethanolamine and derivatives thereof, sodium hydroxide, potassium hydroxide and the compounds of formula (IV) below:

wherein:
W is a propylene residue which may be unsubstituted or substituted with at least one entity chosen from hydroxyl groups and $C_1$-$C_4$ alkyl radicals; and
$R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

The dye composition according to the present disclosure may be in various forms, such as liquids, creams, or gels, or any other form suitable for dyeing keratin fibers, such as human hair.

Also disclosed herein is a method for dyeing keratin fibers comprising applying a composition in accordance with the present disclosure to the keratin fibers, and developing the color by applying an oxidizing agent. The color may be developed at acidic, neutral, or alkaline pH and the oxidizing agent may be added to the composition just at the time of use, or an oxidizing composition comprising at least one oxidizing agent may be applied simultaneously or sequentially to the composition of the present disclosure. In at least one embodiment, this coloration may be developed at neutral pH.

According to one embodiment, the composition of the present disclosure may be mixed, for instance, at the time of use, with a composition comprising, in a medium that is suitable for dyeing, at least one oxidizing agent, this oxidizing agent being present in an amount that is sufficient to develop a coloration. This mixture may then be applied to the keratin fibers. After an action time of 3 to 50 minutes, for example, from 5 to 30 minutes, the keratin fibers may be rinsed, washed with shampoo, rinsed again, and then dried.

The oxidizing agents conventionally used for the oxidation dyeing of keratin fibers include, for example, hydrogen peroxide; urea peroxide; alkali metal bromates; persalts, such as perborates and persulfates; peracids; and oxidase enzymes, for instance, peroxidases, 2-electron oxidoreductases, such as uricases, and 4-electron oxygenases, for instance, laccases. In at least one embodiment, the at least one oxidizing agent may be hydrogen peroxide.

The oxidizing composition may also contain at least one adjuvant conventionally used in compositions for dyeing the hair and as described above.

The pH of the oxidizing composition containing the oxidizing agent may be such that, after mixing with the dye composition, the pH of the resulting composition applied to the keratin fibers ranges, for example, from 3 to 12, for instance, from 5 to 11. The pH may be adjusted to the desired value by means of acidifying or basifying agents conventionally used in the dyeing of keratin fibers and as described above.

The ready-to-use composition that may be applied to the keratin fibers may be in various forms, such as liquids, creams, or gels, or any other form that is suitable for dyeing keratin fibers, such as human hair.

Also disclosed herein is a multi-compartment dyeing device or "kit", comprising at least two compartments, wherein at least one first compartment contains the dye composition of the present disclosure with the exception of the oxidizing agent, and at least one second compartment contains an oxidizing composition. This device may be equipped with a means for applying the desired mixture to the hair, such as the devices described in French Patent No. 2 586 913.

The diamino-N,N-dihydropyrazolone derivatives of formula (I) may be obtained from synthetic intermediates and synthetic routes described in the literature, for example, in *J. Het. Chem.*, 38(3): 613-616 (2001); *Helvetica Chimica Acta*, 33: 1183-1194 (1950); *J. Org. Chem.*, 23: 2029 (1958); *J. Am. Chem. Soc.*, 73: 3240 (1951); *J. Am. Chem. Soc.*, 84: 590 (1962); *Justus Liebig Ann. Chem.*, 686: 134 (1965); *Tetrahedron. Lett.*, 31: 2859-2862 (1973); U.S. Pat. Nos. 4,128,425 and 2,841,584, and the references cited therein.

According to these references, the compounds of formula (I) in which the radicals $R_3$ and $R_4$ are hydrogen may be obtained via the synthetic route represented by scheme A below:

Scheme A

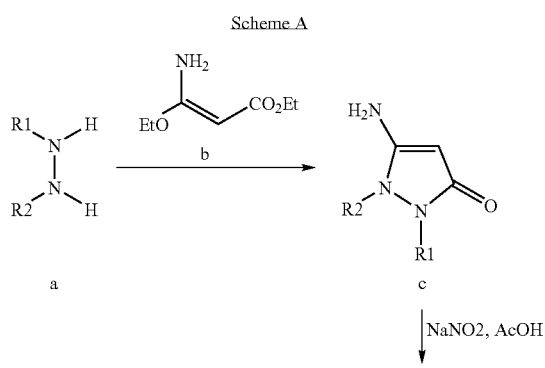

The compounds of formula (I) in which the radicals $R_1$ and $R_2$ are methyl groups and the radicals $R_3$ and $R_4$ are hydrogen may be obtained, for example, by the method described in *Justus Lieb. Ann. Chem.*, 686: 134 (1965) (Scheme B):

Scheme B

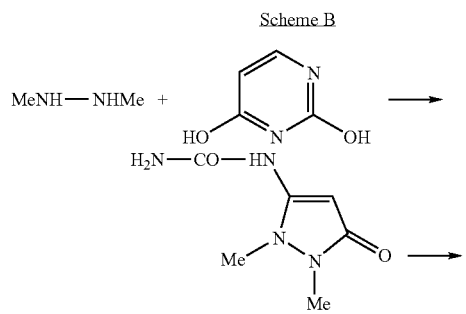

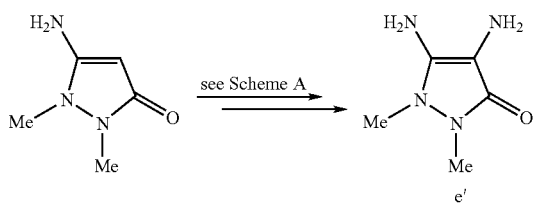

The compounds of formula (I) in which the radical $R_1$ is a methyl group, the radical $R_2$ is a phenyl radical, and the radicals $R_3$ and $R_4$ are hydrogen atoms may be obtained by the method described, for example, in *J. Org. Chem.*, 23: 2029 (1958) and *J. Am. Chem. Soc.*, 73: 3240 (1951) (Scheme C):

Scheme C

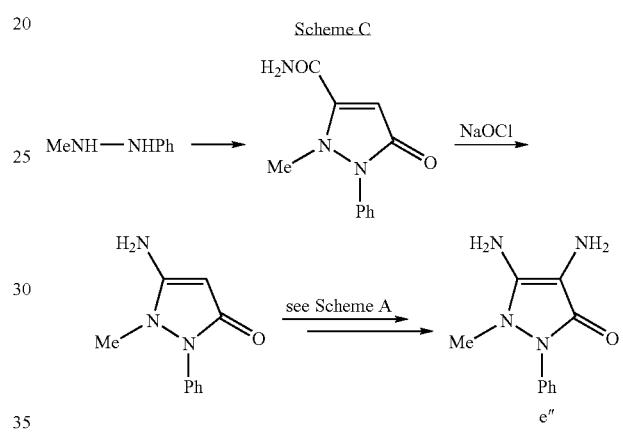

The compounds of formula (I) in which the radicals $R_1$ and $R_2$ together with the nitrogen atoms to which they are attached form a 5-membered ring and in which the radicals $R_3$ and $R_4$ are hydrogen atoms may be obtained, for example, by the method described in *J. Het. Chem.*, 38(3): 613-616 (2001) (Scheme D):

Scheme D

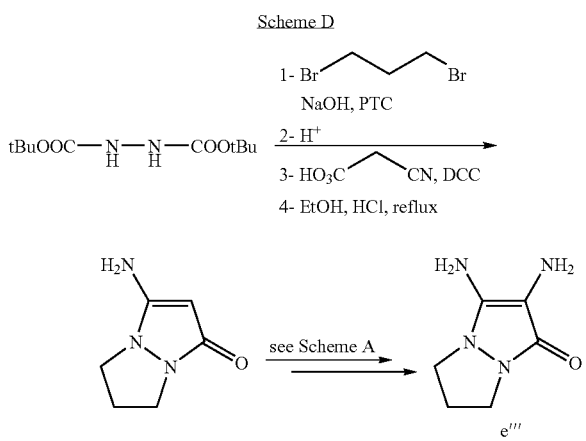

The compounds of formula (I) may also be obtained according to the synthesis illustrated in Scheme E:

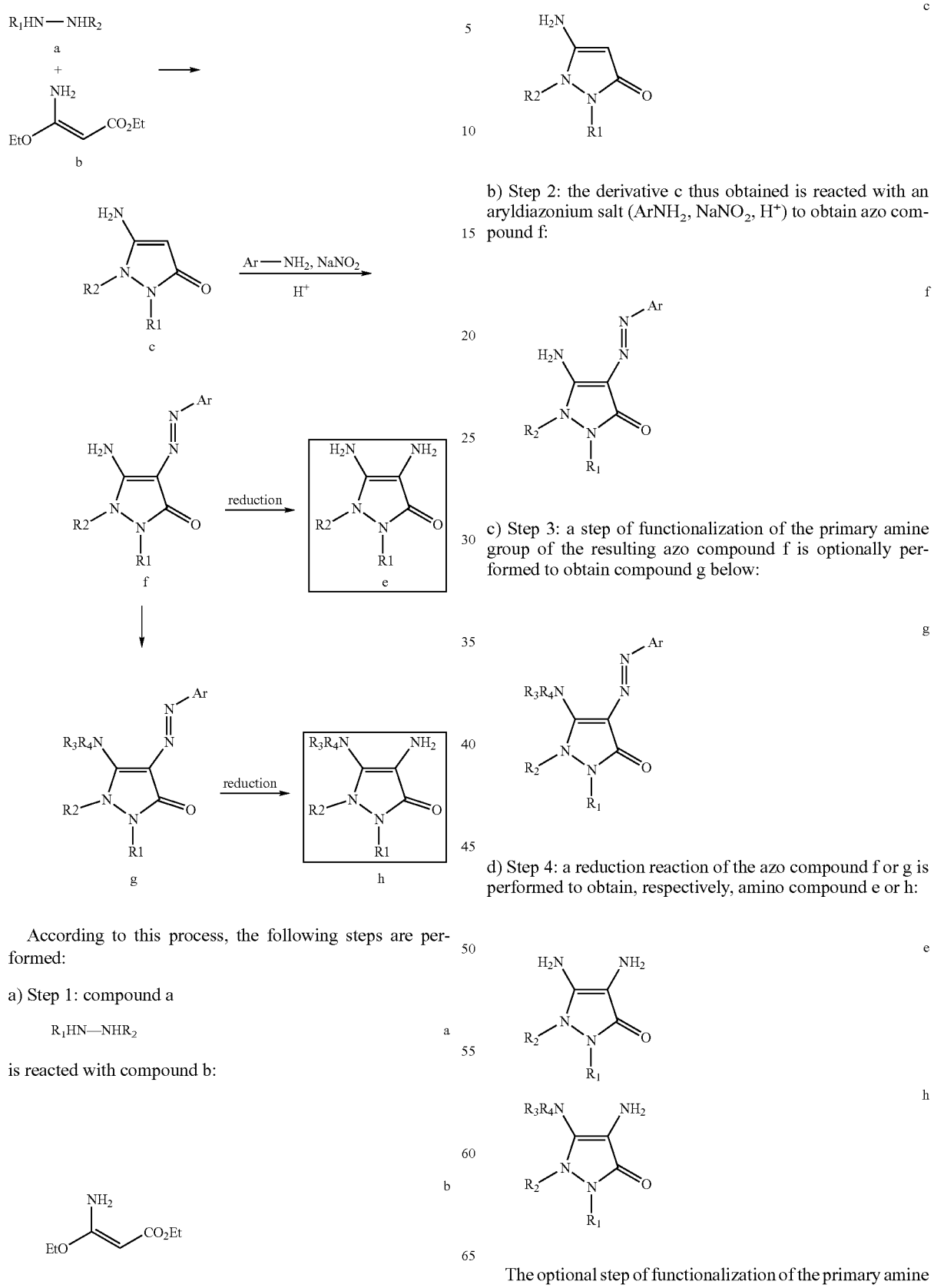

to obtain 5-amino-1,2-dihydropyrazol-3-one (compound c):

b) Step 2: the derivative c thus obtained is reacted with an aryldiazonium salt ($ArNH_2$, $NaNO_2$, $H^+$) to obtain azo compound f:

c) Step 3: a step of functionalization of the primary amine group of the resulting azo compound f is optionally performed to obtain compound g below:

d) Step 4: a reduction reaction of the azo compound f or g is performed to obtain, respectively, amino compound e or h:

According to this process, the following steps are performed:

a) Step 1: compound a $R_1HN\text{—}NHR_2$     a is reacted with compound b:

The optional step of functionalization of the primary amine group in position 5 to a secondary and tertiary amine $NR_3R_4$, to obtain the compound g, is performed according to the standard methods of organic synthesis (alkyl halide, alkyl O-sulfonate, alkyl trialkyl-ammonium, reductive amination, etc., see, for example, J. March, *Advanced Organic Chemistry*, 3rd edition, Wiley Interscience (1985)).

Reduction of the azo group leads to compounds e and h in accordance with the present disclosure.

The reduction step may be performed in a conventional manner, for example, by performing a hydrogenation reaction via heterogeneous catalysis in the presence of Pd/C, Pd(II)/C, Ni/Ra, etc., or alternatively, by performing a reduction reaction with a metal, for example, with zinc, iron, tin, etc. (see, for example, J. March, *Advanced Organic Chemistry*, 3rd edition, Wiley Interscience (1985) and M. Hudlicky, *Reduction in Organic Chemistry*, Ellis Horwood Series Chemical Science (1983)).

According to another process, the 2,3-diamino-6,7-dihydro-1H,5H-pyrazolo[1,2-a]pyrazol-1-one and 2,3-diamino-5,6,7,8-tetrahydro-1H,6H-pyridazino[1,2-a]pyrazol-1-one derivatives may be obtained according to the synthesis illustrated by Scheme F:

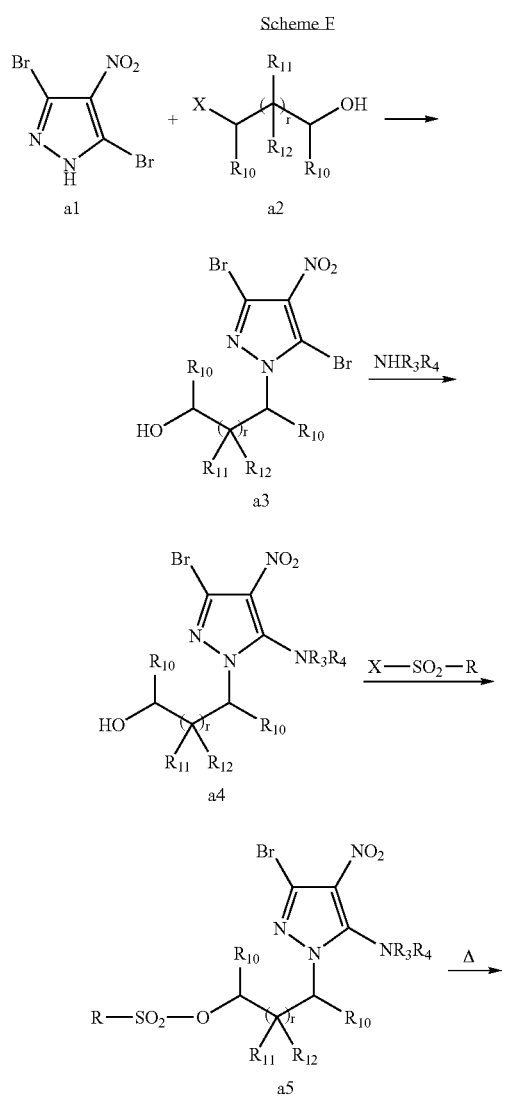

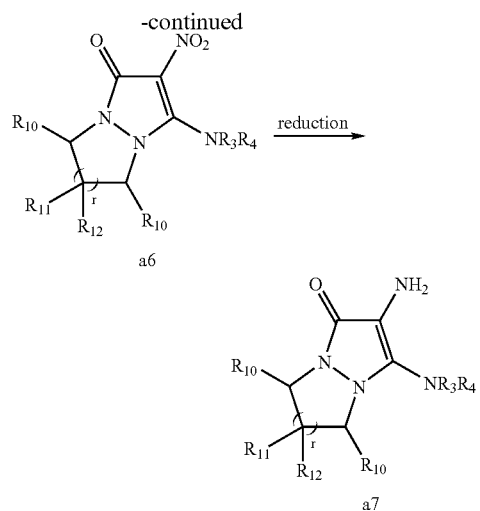

According to this process, the following steps are performed:

a) Step 1: compound a1:

is reacted with compound a2:

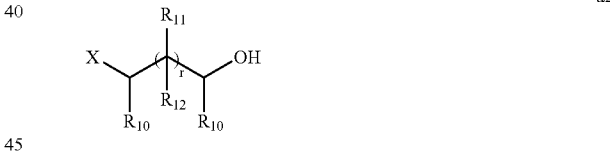

to obtain compound a3:

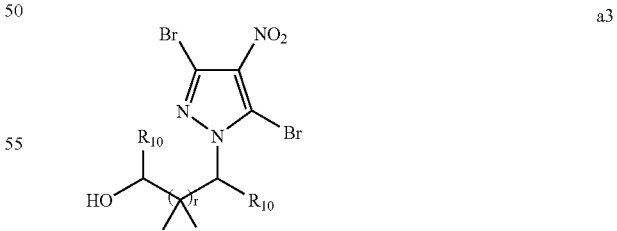

wherein:
the radical $R_{10}$ is chosen from hydrogen; carboxyl radicals; carboxamido radicals; and $C_1$-$C_4$ alkyl radicals optionally substituted with at least one radical chosen from hydroxyl, amino, (di)alkylamino, alkoxy, carboxyl, and sulfonyl radicals;

the radicals $R_{11}$ and $R_{12}$, which may be identical or different, are chosen from hydrogen; halogen atoms; amino radicals; (di)($C_1$-$C_4$)alkylamino radicals; hydroxyl radicals; carboxyl radicals; carboxamido radicals; ($C_1$-$C_2$) alkoxy radicals; and $C_1$-$C_4$ alkyl radicals optionally substituted with at least one radical chosen from hydroxyl, amino, (di)alkylamino, alkoxy, carboxyl, and sulfonyl radicals;

X is chosen from halogen atoms and alkylsulfonates; and r is an integer ranging from 1 to 3.

b) Step 2: compound a3 is reacted with an amine of formula $NHR_3R_4$ to obtain compound a4:

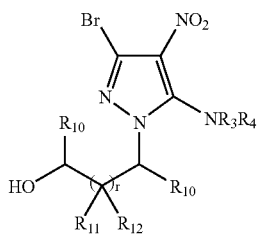

c) Step 3: compound a4 is reacted with at least one halide chosen from alkylsulfonyl, arylsulfonyl, and perfluoroalkylsulfonyl halides R—$O_2$S—$X_1$ (wherein R is chosen from alkyl, aryl, and perfluoroalkyl radicals, and $X_1$ is chosen from halogen atoms), in a solvent with a boiling point ranging from 60° C. to 190° C., to obtain compound a5:

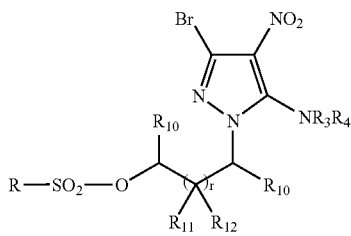

d) Step 4: the resulting compound a5 is then heated in a solvent with a boiling point ranging from 60° C. to 190° C. to obtain compound a6:

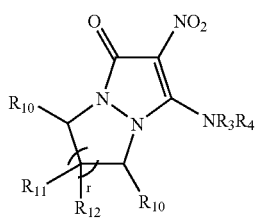

e) Step 5: compound a6 is reduced to obtain compound a7 of formula (V) below:

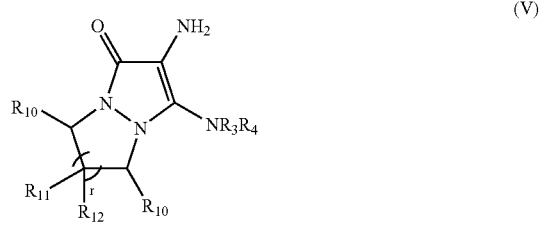

In at least one embodiment, according to this process, the 3,5-dibromo-4-nitropyrazole a1, obtained, for example, according to the method described in German Patent No. 4 234 885, may react with the reagent a2, for instance, in a solvent with a boiling point ranging from 60° C. to 190° C. Examples of suitable solvents include, but are not limited to, pentanol, dimethylformamide, and N-methylpyrrolidine. The reaction, in at least one embodiment, may be performed in the presence of at least one organic or mineral base, for instance, a base chosen from sodium carbonate, sodium hydroxide, sodium acetate, and triethylamine. The temperature of the reaction medium may be maintained at a temperature ranging from 60° C. to 160° C., for example, from 80° C. to 120° C.

The 1-hydroxyalkyl-3,5-dibromo-4-nitropyrazole a3 may be isolated by precipitation or crystallization after addition of ice to the reaction medium.

In step 2, the derivative a3 is reacted with an amine $NHR_3R_4$, for example, in a solvent with a boiling point ranging from 60° C. to 190° C., for instance, butanol, pentanol, or dimethylformamide. The temperature may range from 60° C. to 160° C., for example, from 80° C. to 120° C. After consumption of the reagents, the 5-amino-4-nitro-3-bromo-1-hydroxyalkylpyrazole compound a4 may be isolated by precipitation or crystallization from water.

In step 3, the derivative a5 is obtained by reacting alcohol a4 and a halide chosen from alkylsulfonyl, arylsulfonyl, and perfluoroalkylsulfonyl halides. The reaction may take place in an aprotic solvent, for instance, tetrahydrofuran and dioxane. In one embodiment, the reaction may take place at a temperature ranging from −20° C. to 60° C., for example, from 0° C. to 25° C. Furthermore, this step may take place in the presence of an organic or mineral base, for instance, a base chosen from potassium carbonate, triethylamine, and N-methylmorpholine. After disappearance of the reagents, compound a5 may be isolated by precipitation or crystallization from water.

The sulfonate a5 obtained after step 3 is placed, in step 4, in solution or in dispersion in a solvent with a boiling point ranging from 60° C. to 190° C., for example, from 90° C. to 140° C. The temperature of the reaction medium is then brought to a tempterature ranging from 90° C. to 140° C., for instance, from 105° C. to 125° C. until all of the sulfonate a5 has been consumed. After cooling to room temperature, the perhydropyrazolo[1,2-a]pyrazol-1-one (r=1), perhydropyridazino[1,2-a]pyrazol-1-one (r=2) or perhydrodiazepino[1,2-a]pyrazolone (r=3) compound a6 crystallizes and may be isolated via the standard methods of organic synthesis.

The final compound a7 in accordance with the present disclosure is obtained during step 5, via reduction of the nitro derivative a6, wherein the reduction method may be, for example, a hydrogenation via heterogeneous catalysis in the presence of Pd/C, Pd(II)/C, Ni/Ra, etc., or alternatively, a reduction reaction with a metal, for example, zinc, iron, tin, etc. (see, for example, J. March, *Advanced Organic Chemistry*, 3rd edition, Wiley Interscience (1985) and M. Hudlicky, *Reduction in Organic Chemistry*, Ellis Horwood Series Chemical Science (1983)).

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

Synthesis Examples

Example 1

Synthesis of 2,3-diamino-6,7-dihydro-1H,5H-pyrazolo[1,2-a]pyrazol-1-one dihydrochloride (Compound 5)

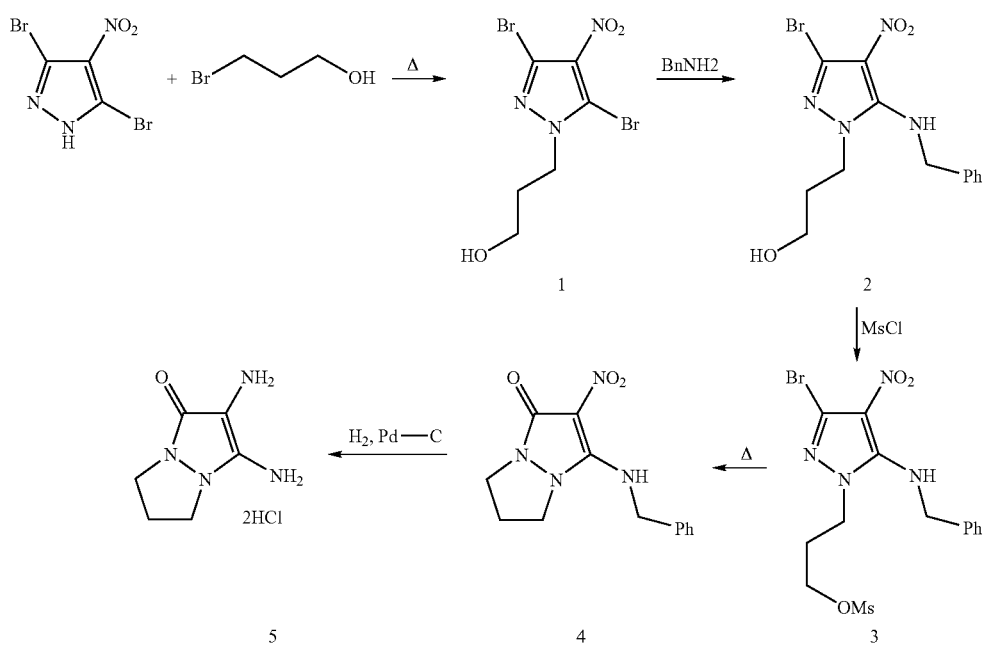

Step 1: Synthesis of 3-(3,5-dibromo-4-nitro-1H-pyrazol-1-yl)propan-1-ol (Compound 1)

0.369 mol of sodium acetate was introduced into a solution of 0.184 mol of dibromonitropyrazole in 250 ml of N-methylpyrrolidone in a 500 ml three-necked flask, and the reaction medium was brought to 80° C.

0.369 mol of 3-bromopropanol was added dropwise at this temperature. This temperature was maintained for 5 hours.

After cooling to room temperature, the medium was poured onto ice with stirring.

The 3-(3,5-dibromo-4-nitro-1H-pyrazol-1-yl)propan-1-ol (compound 1) precipitated. It was filtered off by suction, dried, and obtained in a yield of 75%.

The mass of the expected compound $C_6H_7Br_2N_3O_3$ was detected by mass spectrometry.

The NMR analyses ($^1$H 400 MHz and $^{13}$C 100.61 MHz DMSO $d_6$) were in accordance with the expected structure.

Step 2: Synthesis of 3-[5-(benzylamino)-3-bromo-4-nitro-1H-pyrazol-1-yl]propan-1-ol (Compound 2)

0.135 mol of 3-(3,5-dibromo-4-nitro-1H-pyrazol-1-yl) propan-1-ol (compound 1) was dispersed in a 500 ml three-necked flask containing 150 ml of ethanol. The mixture was heated to 60° C. and 0.825 mol of benzylamine was then added over 30 minutes.

After 6 hours at 60° C., the reaction medium was cooled to room temperature.

The 3-[5-(benzylamino)-3-bromo-4-nitro-1H-pyrazol-1-yl]propan-1-ol (compound 2) was precipitated by pouring the reaction medium onto 1 litre of ice with stirring. After filtration by suction and drying under vacuum in the presence of $P_2O_5$, compound 2 was isolated in a yield of 90%.

The NMR analyses ($^1H$ 400 MHz and $^{13}C$ 100.61 MHz DMSO $d_6$) were in accordance with the expected structure.

Elemental Analysis:

| Theory: | C43.96 | H4.26 | N15.77 | O13.51 | Br22.50 |
|---|---|---|---|---|---|
| Found: | C44.09 | H4.22 | N15.44 | O14.37 | Br21.50 |

Step 3: Synthesis of 3-[5-(benzylamino)-3-bromo-4-nitro-1H-pyrazol-1-yl]propyl methanesulfonate (Compound 3)

0.126 mol of 3-[5-(benzylamino)-3-bromo-4-nitro-1H-pyrazol-1-yl]propan-1-ol (compound 2) and 15.82 mol of triethylamine were introduced, with stirring, into a 500 ml three-necked flask containing 200 ml of THF. The mixture obtained was then cooled to 5° C. and 0.126 mol of mesyl chloride was poured in over 45 minutes.

The reaction medium was maintained at this temperature for 2 hours and the 3-[5-(benzylamino)-3-bromo-4-nitro-1H-pyrazol-1-yl]propyl methanesulfonate (compound 3) was then precipitated by pouring the reaction medium onto 800 ml of ice.

After filtering, the solid was washed thoroughly with water and with diisopropyl ether. Drying was performed under vacuum in the presence of $P_2O_5$. The yield for this step was 94%.

The mass of the expected compound $C_{14}H_{17}BrN_4O_5S$ was detected by mass spectrometry.

The NMR analyses ($^1H$ 400 MHz and $^{13}C$ 100.61 MHz DMSO $d_6$) were in accordance with the expected structure.

Elemental Analysis:

| Theory: | C38.81 | H3.96 | N12.93 | O18.46 | S7.40 | Br18.44 |
|---|---|---|---|---|---|---|
| Found: | C39.03 | H3.91 | N12.83 | O18.52 | S7.29 | Br18.26 |

Step 4: Synthesis of 3-(benzylamino)-2-nitro-6,7-dihydro-1H,5H-pyrazolo[1,2-a]pyrazol-1-one (Compound 4)

0.1 mol of 3-[5-(benzylamino)-3-bromo-4-nitro-1H-pyrazol-1-yl]propyl methanesulfonate 3 was dispersed in a 500 ml three-necked flask containing 300 ml of pentanol, and the reaction medium was maintained at 130° C. for 2 hours.

After cooling to room temperature, the solid formed was filtered off by suction on a sinter funnel, washed with diisopropyl ether, and dried under vacuum in the presence of $P_2O_5$. The 3-(benzylamino)-2-nitro-6,7-dihydro-1H,5H-pyrazolo[1,2-a]pyrazol-1-one (compound 4) was obtained in a yield of 86%.

The NMR analyses ($^1H$ 400 MHz and $^{13}C$ 100.61 MHz DMSO $d_6$) were in accordance with the expected structure.

The mass of the expected compound $C_6H_{11}N_4O$ was detected by mass spectrometry.

Elemental Analysis:

| Theory: | C56.72 | H5.49 | N20.36 | O17.44 |
|---|---|---|---|---|
| Found: | C56.68 | H5.13 | N20.38 | O17.69 |

Step 5: Synthesis of 2,3-diamino-6,7-dihydro-1H,5H-pyrazolo[1,2-a]pyrazol-1-one dihydrochloride (Compound 5)

20 g of 3-(benzylamino)-2-nitro-6,7-dihydro-1H,5H-pyrazolo[1,2-a]pyrazol-1-one (compound 4) and 4 g of 5% palladium-on-charcoal were introduced into a 1 litre autoclave containing 800 ml of ethanol. The reduction was then performed under a hydrogen pressure of 8 bar and at a temperature ranging from 50° C. to 100° C. (with a stirring speed ranging from 1000 to 2500 rpm).

After reaction for 4 hours, there was no further consumption of hydrogen and the medium was cooled to 20° C.

The catalyst was removed under nitrogen by filtration, and hydrochloric ethanol was then added to the filtrate. The crystalline product was filtered off by suction, washed with diisopropyl ether and then dried under vacuum in the presence of $P_2O_5$. The 2,3-diamino-6,7-dihydro-1H,5H-pyrazolo[1,2-a]pyrazol-1-one dihydrochloride (compound 5) was obtained in a yield of 89%.

The mass of the expected compound was detected by mass spectrometry.

The NMR analyses ($^1H$ 400 MHz and $^{13}C$ 100.61 MHz DMSO $d_6$) were in accordance with the expected structure.

Elemental Analysis:

| Theory: | C31.73 | H5.33 | N24.67 | O7.07 | C131.22 |
|---|---|---|---|---|---|
| Found: | C31.45 | H5.20 | N24.62 | O7.24 | C130.86 |

Example 2

Synthesis of 2-amino-3-(ethylamino)-6,7-dihydro-1H,5H-pyrazolo[1,2-a]pyrazol-1-one dihydrochloride (Compound 9)

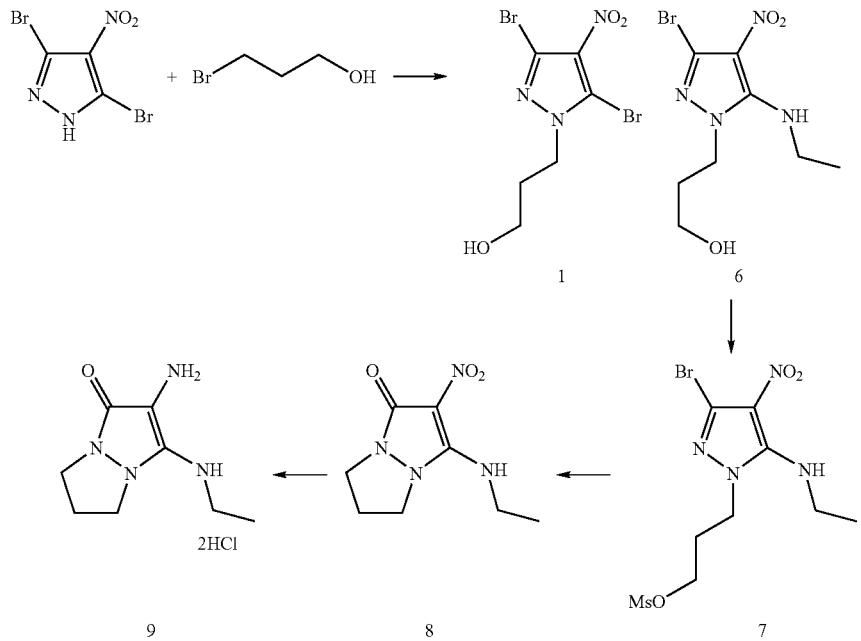

Step 1: Synthesis of 3-(3,5-dibromo-4-nitro-1H-pyrazol-1yl)propan-1-ol (Compound 1)

This step was performed as described above in Example 1.

Step 2: Synthesis of 3-[3-bromo-5-(ethylamino)-4-nitro-1H-pyrazol-1-yl]propan-1-ol (Compound 6)

15 mmol of 3-(3,5-dibromo-4-nitro-1H-pyrazol-1-yl)propan-1-ol were introduced into 30 ml of ethanol in a three-necked flask, with stirring. The homogeneous medium was heated to 75° C. and 93 mmol of ethylamine were then added dropwise and stirring was continued for four hours.

After cooling to room temperature, the medium was poured onto ice and the 3-[3-bromo-5-(ethylamino)-4-nitro-1H-pyrazol-1-yl]propan-1-ol (compound 6) precipitated.

The yellow solid was filtered off by suction and then washed thoroughly with water and diisopropyl ether. Drying was performed under vacuum in the presence of $P_2O_5$. The recovered mass was 3.6 g.

The NMR analyses ($^1H$ 400 MHz and $^{13}C$ 100.61 MHz DMSO $d_6$) were in accordance with the expected structure.

The mass of the expected compound $C_8H_{13}BrN_4O_3$ was detected by mass spectrometry.

Step 3: Synthesis of 3-[5-(ethylamino)-3-bromo-4-nitro-1H-pyrazol-1-yl]propyl methanesulfonate (Compound 7)

11.2 mmol of 3-[3-bromo-5-(ethylamino)-4-nitro-1H-pyrazol-1-yl]propan-1-ol 6 and 1.6 ml of triethylamine were introduced, with stirring, into a 100 ml three-necked flask containing 30 ml of THF. The homogeneous orange mixture obtained was cooled to 0° C. and 1.44 ml of mesyl chloride were added over 20 minutes.

The reaction medium was maintained at this temperature for 2 hours and the 3-[5-(ethylamino)-3-bromo-4-nitro-1H-pyrazol-1-yl]propyl methanesulfonate (compound 7) was precipitated by pouring the reaction medium onto 500 ml of ice.

The yellow solid was filtered by suction and then washed thoroughly with water and diisopropyl ether; drying was performed under vacuum in the presence of $P_2O_5$. The recovered mass was 3.1 g.

The NMR analyses ($^1H$ 400 MHz and $^{13}C$ 100.61 MHz DMSO $d_6$) were in accordance with the expected structure.

The mass of the expected compound $C_9H_{15}BrN_4O_5S$ was detected by mass spectrometry.

Step 4: Synthesis of 3-(ethylamino)-2-nitro-6,7-dihydro-1H,5H-pyrazolo[1,2-a]pyrazol-1-one (Compound 8)

8 mmol of 3-[5-(ethylamino)-3-bromo-4-nitro-1H-pyrazol-1-yl]propyl methanesulfonate (compound 7) were dispersed, with stirring, in a 50 ml three-necked flask containing 20 ml of pentanol, and the reaction medium was maintained at 130° C. for 2 hours.

After cooling to room temperature, the solid formed was filtered off by suction and then washed with diisopropyl ether.

After drying under vacuum in the presence of $P_2O_5$, 1.46 g of 3-(ethylamino)-2-nitro-6,7-dihydro-1H,5H-pyrazolo[1,2-a]pyrazol-1-one (compound 8) were obtained.

The NMR analyses ($^1H$ 400 MHz and $^{13}C$ 100.61 MHz DMSO $d_6$) were in accordance with the expected structure.

The mass of the expected compound was detected by mass spectrometry.

Step 5: Synthesis of 2-amino-3-(ethylamino)-6,7-dihydro-1H,5H-pyrazolo[1,2-a]pyrazol-1-one dihydrochloride (Compound 9)

1.45 g of 3-(ethylamino)-2-nitro-6,7-dihydro-1H,5H-pyrazolo[1,2-a]pyrazol-1-one (compound 8) and 300 mg of 5% palladium-on-charcoal were introduced into a 300 ml autoclave containing 200 ml of ethanol. The reduction was performed at a hydrogen pressure of 8 bar at a temperature of 60° C. (stirring at 1700 rpm).

After reaction for 2 hours, there was no further consumption of hydrogen and the reaction medium was cooled to 20° C.

The catalyst was removed by filtration under nitrogen and the filtrate was diluted with 100 ml of hydrochloric isopropyl ether.

The pale yellow solution was evaporated to dryness and the solid was then taken up in an ethanol/isopropyl ether mixture. The 2-amino-3-(ethylamino)-6,7-dihydro-1H,5H-pyrazolo[1,2-a]pyrazol-1-one hydrochloride (compound 9) precipitated; it was filtered off by suction and, after drying under vacuum in the presence of $P_2O_5$, 1.18 g of 2-amino-3-(ethylamino)-6,7-dihydro-1H,5H-pyrazolo[1,2-a]pyrazol-1-one dihydrochloride (compound 9) were recovered.

The NMR analyses (1H 400 MHz and $^{13}C$ 100.61 MHz DMSO $d_6$) were in accordance with the expected structure.

The mass of the expected compound $C_8H_{14}N_4O$ was detected by mass spectrometry.

Example 3

Synthesis of 2-amino-3-(isopropylamino)-6,7-dihydro-1H,5H-pyrazolo[1,2-a]pyrazol-1-one (Compound 13)

Step 1: Synthesis of 3-(3,5-dibromo-4-nitro-1H-pyrazol-1-yl)propan-1-ol (Compound 1)

This step was performed as described above in Example 1.

Step 2: Synthesis of 3-[3-bromo-5-(isopropylamino)-4-nitro-1H-pyrazol-1-yl]propan-1-ol (Compound 10)

15 mmol of 3-(3,5-dibromo-4-nitro-1H-pyrazol-1-yl)propan-1-ol were introduced, with stirring, into 30 ml of ethanol in a three-necked flask. The homogeneous medium was heated to 75° C. and 93 mmol of isopropylamine were then added dropwise with continued stirring for 4 hours.

After cooling to room temperature, the medium was poured onto ice and then neutralized with hydrochloric acid. The 3-[3-bromo-5-(isopropylamino)-4-nitro-1H-pyrazol-1-yl]propan-1-ol (compound 10) was extracted with dichloromethane.

After drying the organic phase over sodium sulfate and removing the solvent by evaporation under vacuum, 4.37 g of 3-[3-bromo-5-(isopropylamino)-4-nitro-1H-pyrazol-1-yl]propan-1-ol (compound 10) were obtained.

The NMR analyses ($^1H$ 400 MHz and $^{13}C$ 100.61 MHz DMSO $d_6$) were in accordance with the expected structure.

The mass of the expected compound $C_9H_{15}BrN_4O_3$ was detected by mass spectrometry.

Step 3: Synthesis of 3-[5-(isopropylamino)-3-bromo-4-nitro-1H-pyrazol-1-yl]propyl methanesulfonate (Compound 11)

13.7 mmol of 3-[3-bromo-5-(isopropylamino)-4-nitro-1H-pyrazol-1-yl]propan-1-ol (compound 10) and 1.94 ml of triethylamine were introduced, with stirring, into a 50 ml three-necked flask containing 20 ml of THF. The homoge-

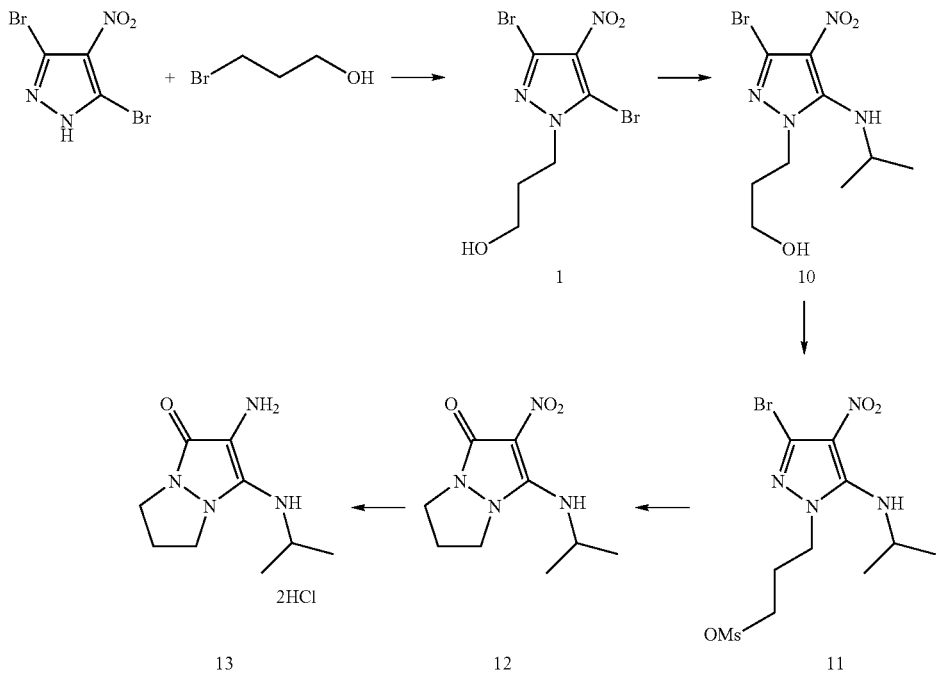

neous orange mixture thus obtained was cooled to 0° C. and 1.76 ml of mesyl chloride were added over 20 minutes.

The reaction medium was maintained at this temperature for 2 hours, and 3-[5-(ethylamino)-3-bromo-4-nitro-1H-pyrazol-1-yl]propyl methanesulfonate (compound 11) was then precipitated by pouring the reaction medium onto 500 ml of ice.

The yellow solid was filtered off by suction and then washed thoroughly with water and petroleum ether, and was dried under vacuum in the presence of $P_2O_5$. The recovered mass was 4.2 g.

The NMR analyses ($^1H$ 400 MHz and $^{13}C$ 100.61 MHz DMSO $d_6$) were in accordance with the expected structure.

The mass of the expected compound was detected by mass spectrometry.

Step 4: Synthesis of 3-(isopropylamino)-2-nitro-6,7-dihydro-1H,5H-pyrazolo[1,2-a]pyrazol-1-one (Compound 12)

10 mmol of 3-[5-(isopropylamino)-3-bromo-4-nitro-1H-pyrazol-1-yl]propyl methanesulfonate (compound 11) were dispersed, with stirring, in 20 ml of pentanol in a 50 ml three-necked flask, and the mixture was heated at 130° C. for 2 hours.

After cooling to room temperature, the solid obtained was filtered off by suction on a sinter funnel and washed with diisopropyl ether.

After drying under vacuum in the presence of $P_2O_5$, 1.71 g of 3-(isopropylamino)-2-nitro-6,7-dihydro-1H,5H-pyrazolo[1,2-a]pyrazol-1-one (compound 12) were obtained.

The NMR analyses ($^1H$ 400 MHz and $^{13}C$ 100.61 MHz DMSO $d_6$) were in accordance with the expected structure.

The mass of the expected compound $C_9H_{14}N_4O_3$ was detected by mass spectrometry.

Step 5: Synthesis of 2-amino-3-(isopropylamino)-6,7-dihydro-1H,5H-pyrazolo[1,2-a]pyrazol-1-one dihydrochloride (Compound 13)

1.70 g of 3-(isopropylaminoamino)-2-nitro-6,7-dihydro-1H,5H-pyrazolo[1,2-a]pyrazol-1-one (compound 12) and 300 mg of 5% palladium-on-charcoal were introduced into a 300 ml autoclave containing 200 ml of ethanol. The reaction was performed at a temperature of 60° C. and at a hydrogen pressure of 6 bar (stirring at 2000 rpm).

After reaction for 2 hours, there was no further consumption of hydrogen, and the medium was cooled to 20° C.

The catalyst was removed by filtration under nitrogen after cooling to room temperature, and hydrochloric isopropyl ether was added.

The pale yellow solution was evaporated to dryness and the solid was then taken up in 50 ml of diisopropyl ether saturated with hydrogen chloride, and the precipitate was recovered by suction filtration. After drying under vacuum in the presence of $P_2O_5$, 1.5 g of 2-amino-3-(isopropylamino)-6,7-dihydro-1H,5H-pyrazolo[1,2-a]pyrazol-1-one dihydrochloride (compound 13) were isolated.

The NMR analyses (1H 400 MHz and $^{13}C$ 100.61 MHz DMSO $d_6$) were in accordance with the expected structure.

The mass of the expected compound $C_9H_{16}N_4O$ was detected by mass spectrometry.

Example 4

2-Amino-3-(pyrrolidin-1-yl)-6,7-dihydro-1H,5H-pyrazolo[1,2-a]pyrazol-1-one dihydrochloride (Compound 17)

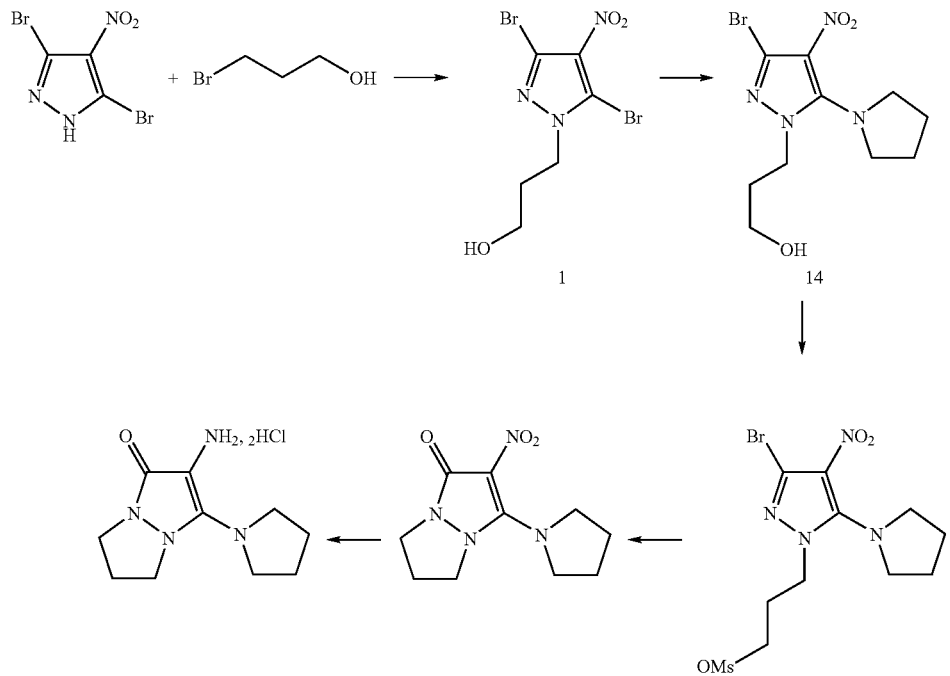

Step 1: Synthesis of 3-(3,5-dibromo-4-nitro-1H-pyrazol-1-yl)propan-1-ol (Compound 1)

This step was performed as described above in Example 1.

Step 2: 3-(3-Bromo-4-nitro-5-(pyrrolidin-1-yl)-1H-pyrazol-1-yl)propan-1-ol (Compound 14)

15 mmol of 3-(3,5-dibromo-4-nitro-1H-pyrazol-1-yl)propan-1-ol were introduced, with stirring, into 20 ml of isopropanol in a three-necked flask. The homogeneous medium was heated to 75° C. and 90 mmol of pyrrolidine were then added dropwise and stirring was continued for 2 hours.

After cooling to room temperature, the medium was poured onto ice and neutralized with hydrochloric acid. The 3-(3-bromo-4-nitro-5-(pyrrolidin-1-yl)-1H-pyrazol-1-yl)propan-1-ol (compound 14) was extracted with dichloromethane.

After drying the organic phase over sodium sulfate and distilling off the solvent by evaporation under vacuum, 4.8 g of 3-(3-bromo-4-nitro-5-(pyrrolidin-1-yl)-1H-pyrazol-1-yl)propan-1-ol (compound 14) were obtained.

The NMR analyses ($^1$H 400 MHz and $^{13}$C 100.61 MHz DMSO $d_6$) were in accordance with the expected structure.

The mass of the expected compound $C_{10}H_{17}BrN_4O$ was detected by mass spectrometry.

Step 3: Synthesis of 3-(3-bromo-4-nitro-5-(pyrrolidin-1-yl)-1H-pyrazol-1-yl)propyl methanesulfonate (Compound 15)

30 mmol of 3-(3-bromo-4-nitro-5-(pyrrolidin-1-yl)-1H-pyrazol-1-yl)propan-1-ol (compound 14) and 4.25 ml of triethylamine were introduced, with stirring, into a 100 ml three-necked flask containing 50 ml of THF. The homogeneous orange mixture obtained was cooled to 0° C. and 2.32 ml of mesyl chloride were added over 20 minutes.

The reaction medium was maintained at this temperature for 2 hours and the 3-(3-bromo-4-nitro-5-(pyrrolidin-1-yl)-1H-pyrazol-1-yl)propyl methanesulfonate (compound 15) was then precipitated by pouring the reaction medium onto ice.

The solid was filtered off by suction and then dried under vacuum in the presence of $P_2O_5$. The recovered mass was 9.3 g.

The NMR analyses ($^1$H 400 MHz and $^{13}$C 100.61 MHz DMSO $d_6$) were in accordance with the expected structure.

The mass of the expected compound $C_{11}H_{19}BrN_4O_3S$ was detected by mass spectrometry.

Step 4: Synthesis of 2-nitro-3-(pyrrolidin-1-yl)-6,7-dihydro-1H,5H-pyrazolo[1,2-a]pyrazol-1-one (Compound 16)

22.5 mmol of 3-(3-bromo-4-nitro-5-(pyrrolidin-1-yl)-1H-pyrazol-1-yl)propyl methanesulfonate (compound 15) were introduced into 100 ml of pentanol, with stirring, in a 250 ml three-necked flask. The medium thus obtained was maintained at 130° C. for 2 hours.

After cooling to room temperature, the 2-nitro-3-(pyrrolidin-1-yl)-6,7-dihydro-1H,5H-pyrazolo[1,2-a]pyrazol-1-one (compound 16) was extracted with dichloromethane.

After drying the organic phase over sodium sulfate and distilling off the solvent under vacuum, 1.2 g of 2-nitro-3-pyrrolidin-1-yl-6,7-dihydro-1H,5H-pyrazolo[1,2-a]pyrazol-1-one (compound 16) were obtained.

The NMR analyses ($^1$H 400 MHz and $^{13}$C 100.61 MHz DMSO $d_6$) were in accordance with the expected structure.

The mass of the expected compound $C_{10}H_{14}N_4O_3$ was detected by mass spectrometry.

Step 5: Synthesis of 2-amino-3-(pyrrolidin-1-yl)-6,7-dihydro-1H,5H-pyrazolo[1,2-a]pyrazol-1-one dihydrochloride (Compound 17)

1.1 g of 2-nitro-3-(pyrrolidin-1-yl)-6,7-dihydro-1H,5H-pyrazolo[1,2-a]pyrazol-1-one (compound 16) and 300 mg of 5% palladium-on-charcoal were introduced into a 300 ml autoclave containing 200 ml of ethanol. The reduction was performed with stirring at 2000 rpm, at a temperature of 60° C. and under a hydrogen pressure of 6 bar.

After reaction for 2 hours, there was no further consumption of hydrogen, and the medium was cooled to 20° C.

The catalyst was removed by filtration under nitrogen after cooling to room temperature, and hydrochloric isopropyl ether was added.

The pale yellow solution was evaporated to dryness and the solid was then taken up in 50 ml of diisopropyl ether saturated with hydrogen chloride, and the precipitate was recovered by suction filtration. After drying under vacuum in the presence of $P_2O_5$, 1.5 g of 2-amino-3-(pyrrolidin-1-yl)-6,7-dihydro-1H,5H-pyrazolo[1,2-a]pyrazol-1-one dihydrochloride (compound 17) were obtained.

The NMR analyses ($^1$H 400 MHz and $^{13}$C 100.61 MHz DMSO $d_6$) were in accordance with the expected structure.

The mass of the expected compound $C_{10}H_{16}N_4O$ was detected by mass spectrometry.

Example 5

Synthesis of 2,3-diamino-6,7-dihydro-1H,5H-pyrazolo[1,2-a]pyrazol-1-one dimethanesulfonate (Compound 3)

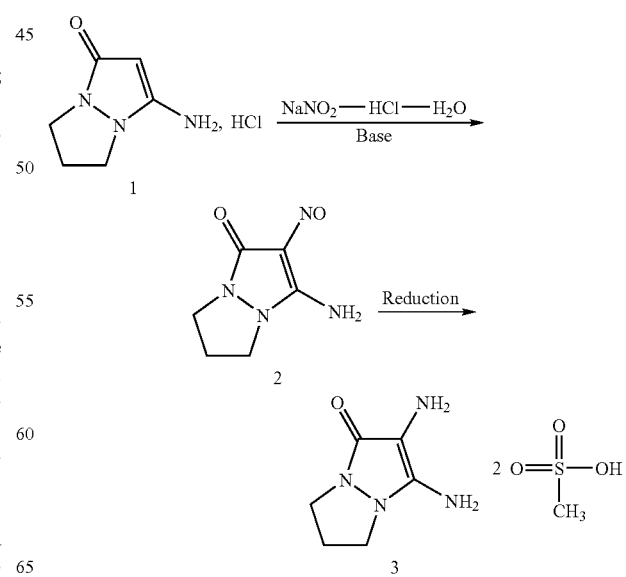

Step 1: Synthesis of 3-amino-2-nitroso-6,7-dihydro-1H,5H-pyrazolo[1,2-a]pyrazol-1-one (Compound 2)

43 g (0.245 mol) of 3-amino-6,7-dihydro-1H,5H-pyrazolo[1,2-a]pyrazol-1-one hydrochloride were dissolved, with stirring, at room temperature, in a mixture of 180 ml of water and 35 ml of 35% hydrochloric acid in a 500 ml three-necked flask.

The mixture was cooled to 0° C. and a solution of 17.3 g of sodium nitrite (0.25 mol) in 20 ml of water was added dropwise over 30 minutes. The temperature of the reaction medium was maintained between 0 and +5° C. throughout the addition and for one hour after the end of the addition.

The reaction medium was brought to pH 8 by adding sodium hydroxide, with stirring, while maintaining the temperature between 0 and 5° C. The 3-amino-2-nitroso-6,7-dihydro-1H,5H-pyrazolo[1,2-a]pyrazol-1-one (compound 2) precipitated in the form of a red-orange solid, which was filtered off on a No. 4 sinter funnel, slurried in a minimum amount of 2-propanol, washed with diisopropyl ether, and dried under vacuum in the presence of phosphorus pentoxide. 35 g of orange-red product were thus obtained (yield: 85%).

The NMR ($^1$H 400 MHz and $^{13}$C 100.61 MHz DMSO d$_6$) and mass spectra were in accordance with the expected structure 2.

Step 2: Synthesis of 2,3-diamino-6,7-dihydro-1H,5H-pyrazolo[1,2-a]pyrazol-1-one dimethanesulfonate (Compound 3)

33.6 g (0.2 mol) of 3-amino-2-nitroso-6,7-dihydro-1H,5H-pyrazolo[1,2-a]pyrazol-1-one (compound 2), 500 ml of ethanol and 6 g of 5% palladium-on-charcoal containing 50% water were introduced into a 1 litre autoclave.

The medium was flushed 3 times with nitrogen and then 3 times with hydrogen and the temperature of the mixture was brought to 40° C.

The reduction was performed over two hours at a pressure of 8 bar. This reduction was exothermic and the temperature spontaneously rose to 70° C.

The temperature was allowed to fall to 50° C. and the catalyst was then filtered off on a filterpress under a stream of nitrogen.

The filtrate was poured into a mixture of 50 ml of ethanol and 40 ml of methanesulfonic acid, with cooling to 0° C. The 2,3-diamino-6,7-dihydro-1H,5H-pyrazolo[1,2-a]pyrazol-1-one dimethanesulfonate (compound 3) crystallized in the form of a pale yellow solid, which was filtered off by suction on a No. 4 sinter funnel, washed with diisopropyl ether and then with petroleum ether, and finally dried under vacuum in the presence of phosphorus pentoxide. 43 g of pale yellow solid were thus obtained (yield: 65%).

The NMR ($^1$H 400 MHz and $^{13}$C 100.61 MHz DMSO d$_6$) and mass spectra were in accordance with the expected structure 3.

Elemental Analysis:

| | | | | | |
|---|---|---|---|---|---|
| Theory: | C27.74 | H5.23 | N16.17 | O32.33 | S18.51 |
| Found: | C27.16 | H5.22 | N15.63 | O32.81 | S18.64 |

Example 6

Synthesis of 2,3-diamino-5,6,7,8-tetrahydro-1H-pyrazolo[1,2-a]pyridazin-1-one hydrochloride (Compound E)

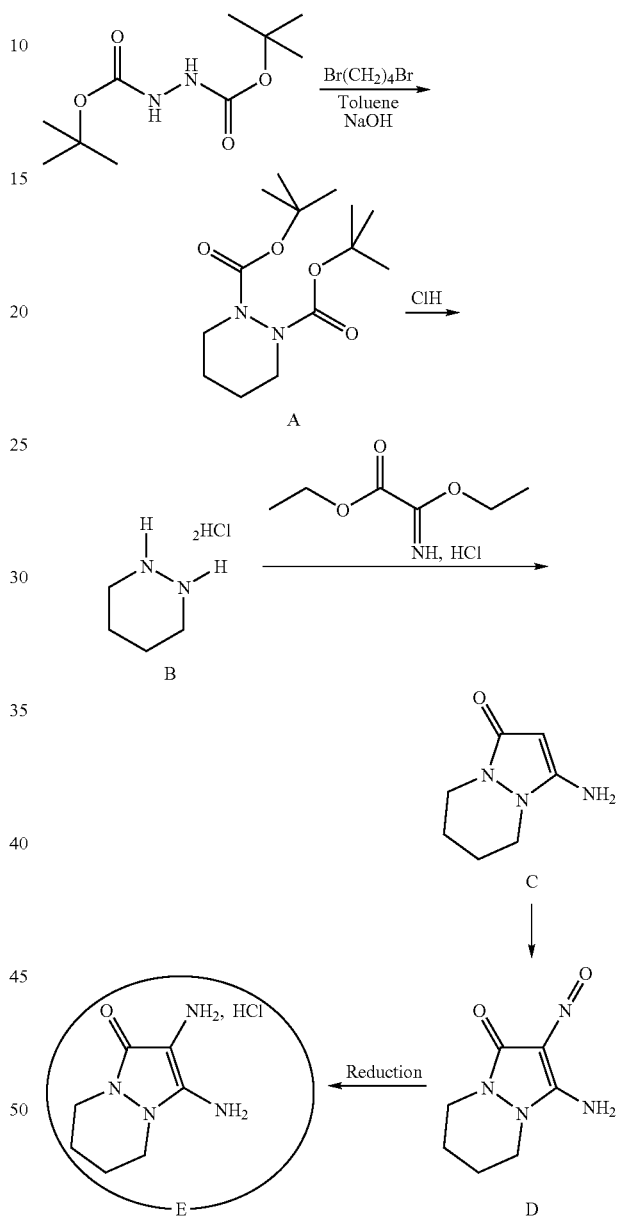

Step 1: Synthesis of di-tert-butyl tetrahydropyridazine-1,2-dicarboxylate (Compound A)

50 ml of toluene, 5 g (21.5 mmol) of N,N'-di-tert-butoxycarbonyl hydrazide, 680 mg of tetraethylammonium bromide and 25 ml of 50% sodium hydroxide were introduced, with mechanical stirring, into a 250 ml three-necked flask equipped with a condenser, a thermometer, and a dropping funnel.

The heterogeneous medium was heated to 100° C. and 1,4-dibromobutane was then added dropwise over 15 minutes.

The reaction medium was heated at 100° C. for 3 days. After cooling, 100 ml of ethyl acetate were added and the mixture was transferred into a separating funnel. The organic phase was washed with 4×70 ml of saturated aqueous sodium carbonate solution and then with 4×70 ml of water, and finally with 4×70 ml of brine. The organic phase was dried over sodium sulfate and the solvent was evaporated off under vacuum. A colorless oil that crystallized as a white solid was thus obtained. A mass of 6.1 g was recovered (yield: 99%).

The NMR ($^1$H 400 MHz and $^{13}$C 100.61 MHz DMSO $d_6$) and mass spectra were in accordance with the expected structure A.

Step 2: Synthesis of hexahydropyridazine dihydrochloride (Compound B)

5.9 g of compound A were introduced into 50 ml of a 3/1 mixture of dioxane and 35% hydrochloric acid, with mechanical stirring, in a 100 ml three-necked flask equipped with a condenser and a thermometer.

The colorless solution obtained was stirred at room temperature for 3 hours and the reaction medium was then diluted with diisopropyl ether. The solvents were evaporated off under vacuum. The pasty residue obtained was taken up in an ether/ethanol mixture. After filtering off the solid and drying under vacuum, 1.39 g of white solid were obtained.

The NMR ($^1$H 400 MHz and $^{13}$C 100.61 MHz DMSO $d_6$) and mass spectra were in accordance with the expected structure B.

Step 3: Synthesis of 3-amino-5,6,7,8-tetrahydro-1H-pyrazolo[1,2-a]pyridazin-1-one (Compound C)

7.5 ml of ethanol, 1.5 ml of triethylamine and 0.73 ml of 3-amino-3-ethoxyacrylic acid were introduced, with mechanical stirring, into a 25 ml three-necked flask equipped with a condenser and a thermometer. 500 mg of hexahydropyridazine dihydrochloride (compound B) were then added and the mixture was stirred for 3 hours at room temperature.

The insoluble material was filtered off and the solvent was distilled off under vacuum. The solid was taken up in a minimum amount of water, filtered off, and dried under vacuum. 0.9 g of a slightly yellow powder was thus obtained.

The NMR ($^1$H 400 MHz and $^{13}$C 100.61 MHz DMSO $d_6$) and mass spectra were in accordance with the expected structure C.

Step 4: Synthesis of 3-amino-2-nitroso-5,6,7,8-tetrahydro-1H-pyrazolo[1,2-a]pyridazin-1-one (Compound D)

20 ml of 35% hydrochloric acid and 1 g of 3-amino-5,6,7,8-tetrahydro-1H-pyrazolo[1,2-a]pyridazin-1-one (compound C) were introduced, with mechanical stirring, into a 50 ml three-necked flask equipped with a condenser and a thermometer.

The mixture was cooled to 0° C. and a solution of 675 mg of sodium nitrite in 5 ml of water was added, while maintaining this temperature. The color of the reaction mixture changed from yellow to orange and a precipitate began to form.

After 30 minutes the reaction was complete, and the orange solid was filtered off on a No. 4 sinter funnel, washed with water, and then dried under vacuum. The yield was 78.3%.

The NMR ($^1$H 400 MHz and $^{13}$C 100.61 MHz DMSO $d_6$) and mass spectra were in accordance with the expected structure D.

Step 5: Synthesis of 2,3-diamino-5,6,7,8-tetrahydro-1H-pyrazolo[1,2-a]pyridazin-1-one hydrochloride (Compound E)

1.3 g of 3-amino-2-nitroso-5,6,7,8-tetrahydro-1H-pyrazolo[1,2-a]pyridazin-1-one (compound D) and 250 mg of 5% palladium-on-charcoal were introduced into a 300 ml autoclave containing 250 ml of ethanol. The reduction was performed with stirring at 2000 rpm, at a temperature of 60° C., and under a hydrogen pressure of 6 bar.

After reaction for 2 hours, there was no further consumption of hydrogen, and the medium was cooled to 20° C.

The catalyst was removed by filtration under nitrogen after cooling to room temperature, and the solution was poured into 75 ml of hydrochloric dioxane.

The solution thus obtained was evaporated until a slightly yellow powder was obtained, which was taken up in diisopropyl ether.

The solid was recovered by filtration. After drying under vacuum in the presence of phosphorus pentoxide, 1.1 g of 2,3-diamino-5,6,7,8-tetrahydro-1H-pyrazolo[1,2-a]pyridazin-1-one dihydrochloride were obtained.

The NMR ($^1$H 400 MHz and $^{13}$C 100.61 MHz DMSO $d_6$) and mass spectra were in accordance with the expected structure E.

Example 7

Synthesis of 4-amino-1,2-diethyl-5-pyrrolidin-1-yl-1,2-dihydropyrazol-3-one hydrochloride

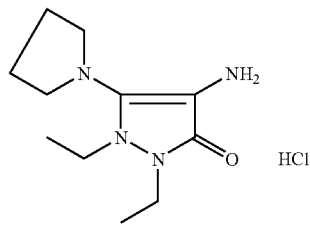

Step 1: Synthesis of 1,2-diethylpyrazolidine-3,5-dione 100 g of diethylhydrazine dihydrochloride (0.63 mol) in 1000 ml of dichloromethane, 85.3 g of malonic acid (0.82 mol; 1.3 eq.), 196 g of hydroxybenzotriazole (1.45 mol; 2.3 eq.), and 278 g of 1-(3-dimethylaminopropyl)-3-ethylcarbodiimide hydrochloride (EDCI; 1.45 mol: 2.3 eq.) were successively introduced, with magnetic stirring, into a 3000 ml three-necked flask under a nitrogen atmosphere, equipped with a thermometer.

The reaction medium was then cooled to between 0° C. and 5° C. 407 g of N,N-diisopropylethylamine (3.14 mol; 520 ml: 5 eq.) are then added slowly thereto. At the end of the addition, the reaction medium, which had become homogeneous, was stirred at room temperature. After being left overnight at room temperature, the reaction was complete.

The reaction medium was washed with 3×600 ml of deionized water. The organic phase was dried over sodium sulfate, filtered, and concentrated under vacuum to give 46 g of crude product. Since the pyrazolidinedione was soluble in aqueous medium, the aqueous phase was thus concentrated to dryness and then taken up in 800 ml of 1N hydrochloric acid solution. The precipitate formed was filtered off and the aqueous phase was extracted with 3×1300 ml of dichloromethane. The combined organic phases were dried over sodium sulfate, filtered, and concentrated under vacuum to give 67.5 g of crude product.

1,2-Diethylpyrazolidine-3,5-dione was thus obtained in the form of a yellow solid in a yield of 40% (39.5 g).

Step 2: Synthesis of 1,2-diethyl-3-chloro-5-pyrazolone 30 g of 1,2-diethylpyrazolidine-3,5-dione (0.19 mol) dissolved in 200 ml of toluene and 35.8 ml of trichlorophosphine oxide (258.9 g; 0.38 mol; 2 eq.) were introduced, under a nitrogen atmosphere, into a 500 ml three-necked flask equipped with a condenser and a magnetic stirrer.

The reaction medium was brought to the reflux temperature of the toluene and the reaction is monitored by TLC (95/5 dichloromethane/methanol). The reaction medium, which was initially in the form of a paste, homogenized as soon as the refluxing started and then became a two-phase mixture.

After refluxing for one hour, the reaction was hydrolyzed at 0° C. by very slow addition of 100 ml of deionized water. After settling of the phases, the toluene phase was separated from the aqueous phase. The aqueous phase was washed with 50 ml of toluene and then brought to pH 12 with 184 ml of 35% sodium hydroxide solution. The formation of a precipitate was observed. The aqueous phase was maintained at 100° C. for 10 minutes and the precipitate dissolved. The reaction medium was then in two phases. The brown-colored upper phase was separated out after settling of the phases while hot. This upper phase was dissolved in 200 ml of dichloromethane, washed once with 50 ml of deionized water, dried over sodium sulfate, and concentrated under vacuum to give 20.5 g of a brown oil.

A precipitate formed in the lower aqueous phase on cooling to room temperature. After filtering off through a sinter funnel, the precipitate was rinsed with water and the filtrate was extracted with 3×300 ml of dichloromethane. The dichloromethane phase was dried over sodium sulfate and concentrated under vacuum to give 5.5 g of brown crystals.

The oil and the brown crystals were collected, grafted on silica, and chromatographed on silica gel (40-60 μm; 2000 g) with an elution gradient:

1) 100 dichloromethane (13 litres)
2) 99.5/0.5 dichloromethane/MeOH (0.8 litre)
3) 99/1 dichloromethane/MeOH (8 litres) expected product +15% impurity m=6.6 g
4) 98.5/1.5 dichloromethane/MeOH (35 litres) expected product (14.7 g).

1,2-Diethyl-3-chloro-5-pyrazolone was thus obtained in the form of yellow crystals in a yield of 44%.

Step 3: Synthesis of 1,2-diethyl-5-pyrrolidin-1-yl-1,2-dihydropyrazol-3-one

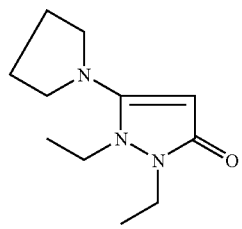

1 g of 5-chloro-1,2-diethyl-1,2-dihydropyrazol-3-one ($5.7 \times 10^{-4}$ mol) was introduced into a 2.5 ml reactor of the Biotage microwave initiator, and 2 ml of pyrrolidine (4.2 eq.) were added thereto.

Operating conditions: microwave at maximum power θ=120° C. for 17 minutes.

After 17 minutes, the reaction was complete (monitoring by TLC, eluent: 90/10 $CH_2Cl_2$/MeOH).

5 ml of demineralized water were then added to the reaction medium, and the assembly was then transferred into a separating funnel. The aqueous phase was extracted with 4×10 ml of dichloromethane. The organic phases were then combined and dried over anhydrous sodium sulfate, and then filtered and evaporated to dryness. 1.2 grams of a brown-orange oil were obtained in a yield of 100%.

NMR ($^1$H 400 MHz DMSO $d_6$) Analysis:
0.81 (1t, 3H), 0.89 (1t, 3H), 1.88 (1m, 1H), 3.22 (1m, 4H), 3.4 (1m, 4H), 4.4 (1s, 1H)

Mass analysis was performed by OpenLynx (FIA/MS). The mass mainly detected was in accordance with the expected structure: M=20.

Step 4: Synthesis of 1,2-diethyl-4-nitroso-5-pyrrolidin-1-yl-1,2-dihydro-3H-pyrazol-3-one

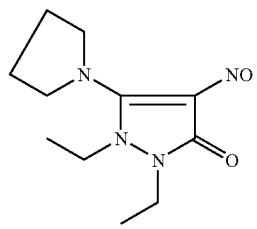

1.2 g of 1,2-diethyl-5-pyrrolidin-1-yl-1,2-dihydropyrazol-3-one were introduced into a fully equipped 25 ml three-necked flask and dissolved in a mixture composed of 0.84 ml of 37% hydrochloric acid and 4 ml of demineralized water.

The reaction medium was cooled to between 0° C. and 5° C. using a bath of ice-water.

A solution of 400 mg of sodium nitrite ($5.7 \times 10^{-4}$ mol) dissolved in 0.6 ml of demineralized water was then added dropwise.

The reaction medium immediately turned bright red as soon as the first drop of the above mixture was added.

After one hour, the reaction was complete.

The pH was adjusted to about 7-8 with 30% sodium hydroxide solution and the reaction medium was then transferred into a separating funnel. The aqueous phase was extracted with 4×10 ml of dichloromethane. The organic phases were combined and dried over anhydrous sodium sulfate and then evaporated to dryness. 1.2 grams of a turquoise-blue powder were obtained in a yield of 89.6%.

The NMR ($^1$H 400 MHz DMSO $d_6$) and mass spectra were in accordance with the expected structure.

NMR ($^1$H 400 MHz DMSO $d_6$) Analysis:

0.94 (1t, 3H), 1 (1t, 3H), 2.05 (1m, 4H), 3.51 (1q, 4H), 3.76 (1q, 4H), 3.94 (1m, 4H)

Mass analysis was performed by OpenLynx (FIA/MS). The mass mainly detected was in accordance with the expected structure. M=238.

Step 5: Synthesis of 4-amino-1,2-diethyl-5-pyrrolidin-1-yl-1,2-dihydropyrazol-3-one hydrochloride 4 grams of zinc powder (0.06 mol) were introduced into 300 ml of absolute ethanol in a fully equipped 500 ml three-necked flask, and 1 ml of acetic acid was added thereto.

The reaction medium was heated to 40° C. and 1.15 g ($4.8 \times 10^{-3}$ mol) of 1,2-diethyl-4-nitroso-5-pyrrolidin-1-yl-1,2-dihydro-3H-pyrazol-3-one were then introduced in spatula portions. 4 ml of acetic acid were finally introduced millilitre by millilitre and the medium was brought to reflux. The medium was fully soluble and colorless. After 30 minutes, the reaction was complete on TLC according to the eluent 90/10 ethyl acetate/MeOH.

The reaction medium was cooled and then filtered on a sinter funnel containing a bed of Celite 545. The mother liquors were filtered into a round-bottomed flask containing 2.5 ml of cooled 5N hydrochloric isopropanol. The mixture was then evaporated to dryness. The product obtained was a pink powder that was in accordance by NMR and Mass.

NMR ($^1$H 400 MHz DMSO $d_6$) Analysis:

0.79 (1t, 3H), 0.96 (1t, 3H), 1.87 (1m, 4H), 3.49 (1q, 2H), 3.59 (1m, 6H)

FIA/MS analysis was performed via OpenLynx. The quasi-molecular ions $[M+H]^+$, $[M+Na]^+$, $[2M+H]^+$, and $[2M+Na]^+$ of the expected base $C_{11}H_{20}N_4O$ were mainly detected.

By repeating the above steps with the appropriate reagents, 4-amino-5-[3-(dimethylamino)pyrrolidin-1-yl]-1,2-diethyl-1,2-dihydro-3H-pyrazol-3-one hydrochloride may be obtained.

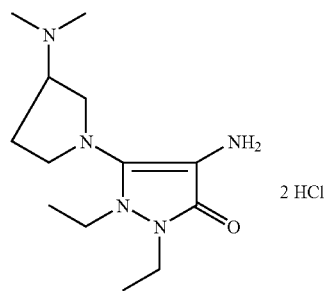

2 HCl

Dyeing Examples

Example 1

Composition 1 was prepared by combining the following components:

| | |
|---|---|
| Lauryl ether carboxylic acid 4.5 EO: | |
| Akypo ® RLM 45 sold by the company Chem Y | 7 g |
| Lauryl alcohol 2 EO: | |
| Dehydol ® LS-2-DEO-N sold by the company Cognis | 4 g |
| Decyl alcohol 5 EO: | |
| Empilan ® KA-5/90-FL sold by the company Albright & Wilson | 8 g |
| Oleyl alcohol | 3 g |
| ($C_{13}/C_{15}$)Alkyl ether carboxylic acid monoethanolamide containing 2 mol of ethylene oxide | 5 g |
| Cationic associative polymer: | |
| Quatrisoft LM 200 ® sold by the company Amerchol | 1 g |
| Monoethanolamine | 2 g |
| Polyquaternium-6: | |
| Merquat ® 100 sold by the company Calgon | 1.5 g |
| Ethanol | 11 g |
| Propylene glycol | 5 g |
| Glycerol | 5 g |
| 2,3-Diamino-6,7-dihydro-1H,5H-pyrazolo[1,2-a]pyrazol-1-one, HCl | 2.27 g |
| 1-Methyl-2-hydroxy-4-aminobenzene | 1.23 g |
| Reducing agents, antioxidants | qs |
| Sequestrants | qs |
| Fragrance | qs |
| Aqueous ammonia (containing 20.5% ammonia) | 1.6 g |
| Demineralized water | qs 100 g |

Mode of Application

At the time of use, composition 1 was mixed with 1.5 times its volume of a 20-volumes hydrogen peroxide solution (6% by weight), the pH of which was equal to 3. A final pH of 9.8 was obtained.

The mixture thus obtained was applied to locks of natural grey hair containing 90% white hairs, in a proportion of 30 g of mixture per 3 g of hair. After a leave-in time of 30 minutes at room temperature, the locks were rinsed, washed with a standard shampoo, rinsed again, and then dried.

The hair coloration was evaluated visually.

| | Tone depth | Tint |
|---|---|---|
| Composition 1 | Dark blond | Strong golden coppery |

Example 2

Composition 2 was prepared by combining the following components:

| | |
|---|---|
| (68/26/60 $C_{12}/C_{14}/C_{16}$) Alkyl polyglucoside as an aqueous 50% solution | 7 g AM |
| Lauryl alcohol 2 EO: | |
| Dehydol ® LS-2-DEO-N sold by the company Cognis | 4 g |
| Decyl alcohol 5 EO: | |
| Empilan ® KA-5/90-FL sold by the company Albright & Wilson | 8 g |
| Oleyl alcohol | 3 g |

-continued

| | |
|---|---|
| ($C_{13}/C_{15}$)Alkyl ether carboxylic acid monoethanolamide containing 2 mol of ethylene oxide | 5 g |
| Cationic associative polymer: | |
| Quatrisoft LM 200 ® sold by the company Amerchol | 1 g AM |
| Monoethanolamine | 2 g |
| Polyquaternium-6: | |
| Merquat ® 100 sold by the company Calgon | 1.5 g |
| Ethanol | 11 g |
| Propylene glycol | 5 g |
| Dipropylene glycerol | 5 g |
| 2,3-Diamino-6,7-dihydro-1H,5H-pyrazolo[1,2-a]pyrazol-1-one, HCl | 1.816 g |
| 6-Hydroxybenzomorpholine | 1.208 g |
| Reducing agents, antioxidants | qs |
| Sequestrants | qs |
| Fragrance | qs |
| Aqueous ammonia (containing 20.5% ammonia) | 1.6 g |
| Demineralized water | qs 100 g |

Mode of Application

At the time of use, composition 2 was mixed with 1.5 times its volume of a 20-volumes hydrogen peroxide solution (6% by weight), the pH of which was equal to 3. A final pH of 9.8 was obtained.

The mixture thus obtained was applied to locks of natural grey hair containing 90% white hairs in a proportion of 30 g of mixture per 3 g of hair. After a leave-in time of 30 minutes at room temperature, the locks were rinsed, washed with a standard shampoo, rinsed again, and then dried.

The hair coloration was evaluated visually.

| | Tone depth | Tint |
|---|---|---|
| Composition 2 | Dark blond | Iridescent red |

Example 3

Composition 3 was prepared by combining the following components:

| | |
|---|---|
| Mixture of linear $C_{18}$ to $C_{24}$ alcohols [7/58/30/6 $C_{18}/C_{20}/C_{22}/C_{24}$, alcohol content > 95%] | 3 g |
| Mixture of linear $C_{18}$ to $C_{24}$ alcohols [7/58/30/6 $C_{18}/C_{20}/C_{22}/C_{24}$, alcohol content > 95%] polyglycerolated with 6 mol of glycerol | 1.35 g |
| Cetearyl alcohol polyglycerolated with 2 mol of glycerol | 4 g |
| Cetearyl alcohol polyglycerolated with 6 mol of glycerol | 2 g |
| Oleic acid | 2.6 g |
| Glycol distearate | 2 g |
| Propylene glycol | 7.5 g |
| Coconut acid monoisopropanolamide | 2 g |
| Aculyn 22 sold by the company Röhm & Haas | 1.4 g AM |
| Crosslinked polyacrylic acid | 0.6 g |
| Cationic polymer* | 3 g AM |
| Merquat ® 100 sold by the company Calgon | 0.4 g AM |
| Reducing agents | 0.7 g |
| Sequestrants | 0.2 g |
| 2,3-Diamino-6,7-dihydro-1H,5H-pyrazolo[1,2-a]pyrazol-1-one, HCl | 2.27 g |
| meta-Aminophenol | 1.09 g |
| Pure monoethanolamine | 1.06 g |

-continued

| | |
|---|---|
| Aqueous ammonia (containing 20.5% ammonia) | 11.1 g |
| Demineralized water | qs 100 g |

*Cationic polymer comprising the sequence of units:

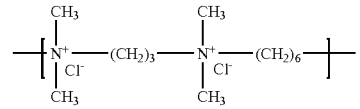

Mode of Application

At the time of use, composition 3 was mixed with 1.5 times its volume of a 25-volumes hydrogen peroxide solution, the pH of which was equal to 3. A final pH of 9.8 was obtained.

The mixture thus obtained was applied to locks of natural grey hair containing 90 white hairs, at a rate of 30 g of mixture per 3 g of hair. After a leave-in time of 30 minutes at room temperature, the locks were rinsed, washed with a standard shampoo, rinsed again, and then dried.

The hair coloration was evaluated visually.

| | Tone depth | Tint |
|---|---|---|
| Composition 3 | Dark blond | Red coppery |

Example 4

Composition 4 was prepared by combining the following components:

| | |
|---|---|
| Mixture of linear $C_{18}$ to $C_{24}$ alcohols [7/58/30/6 $C_{18}/C_{20}/C_{22}/C_{24}$, alcohol content > 95%] | 3 g |
| Mixture of linear $C_{18}$ to $C_{24}$ alcohols [7/58/30/6 $C_{18}/C_{20}/C_{22}/C_{24}$, alcohol content > 95%] polyglycerolated with 6 mol of glycerol | 1.35 g |
| Cetearyl alcohol polyglycerolated with 2 mol of glycerol | 4 g |
| Cetearyl alcohol polyglycerolated with 6 mol of glycerol | 2 g |
| Oleic acid | 2.6 g |
| Glycol distearate | 2 g |
| Propylene glycol | 7.5 g |
| Coconut acid monoisopropanolamide | 2 g |
| Aculyn 22 sold by the company Röhm & Haas | 1.4 g AM |
| Crosslinked polyacrylic acid | 0.6 g |
| Cationic polymer* | 3 g AM |
| Merquat ® 100 sold by the company Calgon | 0.4 g AM |
| Reducing agents | 0.7 g |
| Sequestrants | 0.2 g |
| 2,3-Diamino-6,7-dihydro-1H,5H-pyrazolo[1,2-a]pyrazol-1-one, HCl | 1.56 g |
| 4-Amino-2-hydroxytoluene | 0.28 g |
| 2-Methyl-5-hydroxyethylaminophenol | 0.38 g |
| Pure monoethanolamine | 1.06 g |
| Citric acid | 0.15 g |
| Demineralized water | qs 100 g |

*Cationic polymer comprising the sequence of units:

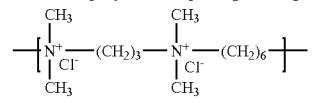

Mode of Application

At the time of use, composition 4 was mixed with 1.5 times its volume of a 25-volumes hydrogen peroxide solution, the pH of which was equal to 3. A final pH of 6.8 was obtained.

The mixture thus obtained was applied to locks of natural grey hair containing 90% white hairs, at a rate of 30 g of mixture per 3 g of hair. After a leave-in time of 30 minutes at room temperature, the locks were rinsed, washed with a standard shampoo, rinsed again, and then dried.

The hair coloration was evaluated visually.

|  | Tone depth | Tint |
| --- | --- | --- |
| Composition 4 | Light blond | Golden coppery |

What is claimed is:

1. A composition for dyeing keratin fibers, comprising, in a suitable medium:
(a) at least one oxidation base chosen from diamino-N,N-dihydropyrazolone derivatives of formula (I) and addition salts thereof:

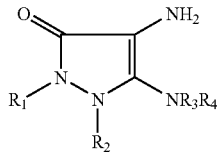

(I)

wherein:
$R_1$, $R_2$, $R_3$, and $R_4$, which may be identical or different, are chosen from:
linear or branched $C_1$-$C_{10}$ alkyl radicals optionally substituted with at least one radical chosen from $OR_5$ radicals, $NR_6R_7$ radicals, carboxyl radicals, sulfonic radicals, carboxamido radicals $CONR_6R_7$, sulfonamido radicals $SO_2NR_6R_7$, and heteroaryl and aryl radicals optionally substituted with at least one group chosen from ($C_1$-$C_4$)alkyl, hydroxyl, $C_1$-$C_2$ alkoxy, amino, and (di)($C_1$-$C_2$)alkylamino groups;
aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals; and
5- or 6-membered heteroaryl radicals, optionally substituted with at least one radical chosen from ($C_1$-$C_4$)alkyl and ($C_1$-$C_2$)alkoxy radicals;
$R_3$ and $R_4$ may also be hydrogen atom;
$R_5$, $R_6$, and $R_7$, which may be identical or different, are chosen from:
hydrogen;
linear or branched $C_1$-$C_4$ alkyl radicals optionally substituted with at least one radical chosen from hydroxyl radicals, $C_1$-$C_2$ alkoxy radicals, carboxamido $CONR_8R_9$ radicals, sulfonyl $SO_2R_8$ radicals, and aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals; and aryl radicals optionally substituted with at least one radical chosen from ($C_1$-$C_4$)alkyl, hydroxyl, $C_1$-$C_2$ alkoxy, amino, and (di)($C_1$-$C_2$) alkylamino radicals;
$R_6$ and $R_7$, which may be identical or different, may also be chosen from carboxamido radicals $CONR_8R_9$ and sulfonyl radicals $SO_2R_8$;
$R_8$ and $R_9$, which may be identical or different, are chosen from hydrogen and linear or branched $C_1$-$C_4$ alkyl radicals optionally substituted with at least one radical chosen from hydroxyl and $C_1$-$C_2$ alkoxy radicals;
$R_1$ and $R_2$, and $R_3$ and $R_4$, may form, together with the nitrogen atoms to which they are attached, a ring chosen from saturated or unsaturated 5- to 7-membered heterocycles optionally substituted with at least one entity chosen from halogen atoms, amino radicals, (di)($C_1$-$C_4$)alkylamino radicals, hydroxyl radicals, carboxyl radicals, carboxamido radicals, ($C_1$-$C_2$)alkoxy radicals, and $C_1$-$C_4$ alkyl radicals optionally substituted with at least one radical chosen from hydroxyl, amino, (di)alkylamino, alkoxy, carboxyl, and sulfonyl radicals;
$R_3$ and $R_4$ may also form, together with the nitrogen atom to which they are attached, a 5- or 7-membered heterocycle, the carbon atoms of which may be replaced with at least one entity chosen from optionally substituted oxygen and nitrogen atoms;
(b) at least one coupler; and
(c) at least one surfactant chosen from ($C_8$-$C_{30}$)alkyl ether carboxylic acids and salts thereof, ($C_{12}$-$C_{30}$)alkyl polyglucosides, monoglycerolated surfactants, and polyglycerolated surfactants.

2. The composition of claim 1, wherein $R_1$ and $R_2$, which may be identical or different, are chosen from $C_1$-$C_6$ alkyl radicals optionally substituted with at least one radical chosen from hydroxyl, ($C_1$-$C_2$)alkoxy, amino, and (di)($C_1$-$C_2$)alkylamino radicals; phenyl radicals; methoxyphenyl radicals; ethoxyphenyl radicals; and benzyl radicals.

3. The composition of claim 2, wherein $R_1$ and $R_2$, which may be identical or different, are chosen from methyl, ethyl, 2-hydroxyethyl, 3-hydroxypropyl, 2-hydroxypropyl, and phenyl radicals.

4. The composition of claim 1, wherein $R_1$ and $R_2$ form, together with the nitrogen atoms to which they are attached, a saturated or unsaturated, optionally substituted 5- or 6-membered ring.

5. The composition of claim 1, wherein $R_1$ and $R_2$ form, together with the nitrogen atoms to which they are attached, a ring chosen from pyrazolidine and pyridazolidine rings, optionally substituted with at least one radical chosen from $C_1$-$C_4$ alkyl, hydroxyl, ($C_1$-$C_2$)alkoxy, carboxyl, carboxamido, amino, and (di)($C_1$-$C_2$)alkylamino radicals.

6. The composition of claim 1, wherein $R_1$ and $R_2$ form, together with the nitrogen atoms to which they are attached, a ring chosen from pyrazolidine and pyridazolidine rings.

7. The composition of claim 1, wherein $R_3$ and $R_4$, which may be identical or different, are chosen from hydrogen; linear or branched $C_1$-$C_6$ alkyl radicals optionally substituted with at least one radical chosen from hydroxyl, ($C_1$-$C_2$) alkoxy, amino, and (di)($C_1$-$C_2$)alkylamino radicals; and phenyl radicals optionally substituted with at least one radical chosen from hydroxyl, amino, and ($C_1$-$C_2$)alkoxy radicals.

8. The composition of claim 1, wherein $R_3$ and $R_4$, which may be identical or different, are chosen from hydrogen, methyl radicals, ethyl radicals, isopropyl radicals, 2-hydroxyethyl radicals, 3-hydroxypropyl radicals, 2-hydroxypropyl radicals, and 2-carboxyethyl radicals.

9. The composition of claim 8, wherein $R_3$ and $R_4$ are hydrogen.

10. The composition of claim 1, wherein $R_3$ and $R_4$ form, together with the nitrogen atom to which they are attached, a 5- or 7-membered ring chosen from pyrrolidine, piperidine, homopiperidine, piperazine, and homopiperazine heterocycles; said rings possibly being substituted with at least one radical chosen from hydroxyl, amino, (di)($C_1$-$C_2$)alkylamino, carboxyl, carboxamido, and $C_1$-$C_4$ alkyl radicals optionally substituted with at least one radical chosen from hydroxyl, amino, and $C_1$-$C_2$ (di)alkylamino radicals.

11. The composition of claim 1, wherein $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, and N-(2-hydroxyethyl)homopiperazine.

12. The composition of claim 1, wherein $R_3$ and $R_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-β-hydroxyethylhomopiperazine.

13. The composition of claim 1, wherein $R_3$ and $R_4$ form, together with the nitrogen atom to which they are attached, a 5-membered ring chosen from pyrrolidine, 3-hydroxypyrrolidine, 3-aminopyrrolidine, and 3-dimethylaminopyrrolidine.

14. The composition of claim 1, wherein the at least one oxidation base is chosen from:
2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-di-(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one; and
2,3-diamino-6-hydroxy-6,7-dihydro-1H,5H-pyrazolo[1,2-a]pyrazol-1-one.

15. The composition of claim 1, wherein the at least one coupler is chosen from meta-phenylenediamines, meta-aminophenols, meta-diphenols, naphthalene-based couplers, heterocyclic couplers, and the addition salts thereof.

16. The composition of claim 15, wherein the at least one coupler is chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

17. The composition of claim 1, wherein the at least one coupler is present in the dye composition in an amount ranging from 0.001% to 10% by weight relative to the total weight of the dye composition.

18. The composition of claim 1, wherein the alkyl ether carboxylic acids and salts thereof are chosen from compounds of formula (II):

wherein:
R is chosen from linear or branched $C_{8-22}$ alkyl and alkylene radicals and ($C_8$-$C_9$)alkylaryl radicals;
A is chosen from oxygen, —CO—, —NH—, and —CO—O—;
B is chosen from random sequences and blocks of p units —$C_3H_6O$— and n units —$C_2H_4O$—;
n is an integer ranging from 1 to 30;
p is an integer ranging from 0 to 15;
q is an integer equal to 0 or 1; and
X is chosen from hydrogen, Na, K, Li, ½ Mg, monoethanolamine residues, ammonium residues, and triethanolamine residues.

19. The composition of claim 18, wherein R is chosen from $C_8$-$C_{22}$ alkyl radicals, A is oxygen, X is chosen from hydrogen and sodium, p is equal to 0, n is an integer ranging from 1 to 20, and q is equal to 0 or 1.

20. The composition of claim 1, wherein the alkyl polyglucosides are chosen from compounds of formula (III):

wherein:
$R'_1$ is chosen from linear or branched alkyl and/or alkylene radicals comprising from 12 to 30 carbon atoms, and alkylphenyl radicals in which the alkyl radical may be linear or branched and comprises from 12 to 30 carbon atoms,
$R'_2$ is chosen from alkylene radicals comprising from 2 to 4 carbon atoms,
G is a sugar comprising from 5 to 6 carbon atoms,
t is a number ranging from 0 to 10, and
v is a number ranging from 1 to 15.

21. The composition of claim 1, wherein the monoglycerolated and polyglycerolated surfactants are chosen from compounds of the following formulae:

R'O[CH$_2$CH(CH$_2$OH)O]$_m$H; R'O[CH$_2$CH(OH)CH$_2$O]$_m$H or R'O[CH(CH$_2$OH)CH$_2$O]$_m$H;

wherein R' is a linear or branched, saturated or unsaturated hydrocarbon-based radical comprising from 8 to 40 carbon atoms; and m is a number ranging from 1 to 30.

22. The composition of claim 21, wherein R' comprises heteroatoms.

23. The composition of claim 21, wherein R' is chosen from an optionally monohydroxylated or polyhydroxylated $C_{10}$-$C_{20}$ alkyl and alkylene radicals.

24. The composition of claim 1, wherein the at least one surfactant is chosen from lauryl ether carboxylic acid, (68/26/6 $C_{12}/C_{14}/C_{16}$)alkyl polyglucoside, and cetearyl alcohol polyglycerolated with r moles of glycerol, r being an integer ranging from 2 to 10.

25. The composition of claim 1, wherein the at least one surfactant is present in the dye composition in an amount ranging from 0.01% to 30% by weight relative to the total weight of the dye composition.

26. The composition of claim 1, further comprising at least one additional oxidation base chosen from para-phenylenediamines, bis(phenyl)alkylenediamines, para-aminophenols, bis-para-aminophenols, ortho-aminophenols, ortho-phenylenediamines, heterocyclic bases other than the derivatives of formula (I), the addition salts thereof, and mixtures thereof.

27. The composition of claim 1, wherein the at least one oxidation base is present in the dye composition in an amount ranging from 0.001% to 10% by weight relative to the total weight of the dye composition.

28. The composition of claim 1, further comprising at least one oxidizing agent.

29. A method for dyeing keratin fibers, comprising applying a dye composition to the keratin fibers in the presence of an oxidizing agent for a time that is sufficient to develop a desired coloration;
wherein the dye composition comprises, in a suitable medium:
(a) at least one oxidation base chosen from diamino-N,N-dihydropyrazolone derivatives of formula (I) and addition salts thereofs:

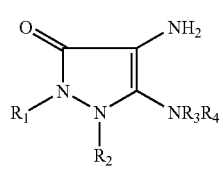

(I)

wherein:
$R_1$, $R_2$, $R_3$, and $R_4$, which may be identical or different, are chosen from:
linear or branched $C_1$-$C_{10}$ alkyl radicals optionally substituted with at least one radical chosen from $OR_5$ radicals, $NR_6R_7$ radicals, carboxyl radicals, sulfonic radicals, carboxamido radicals $CONR_6R_7$, sulfonamido radicals $SO_2NR_6R_7$, and heteroaryl and aryl radicals optionally substituted with at least one group chosen from ($C_1$-$C_4$)alkyl, hydroxyl, $C_1$-$C_2$ alkoxy, amino, and (di)($C_1$-$C_2$)alkylamino groups;
aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals; and
5- or 6-membered heteroaryl radicals, optionally substituted with at least one radical chosen from ($C_1$-$C_4$)alkyl and ($C_1$-$C_2$)alkoxy radicals;
$R_3$ and $R_4$ may also be hydrogen atom;
$R_5$, $R_6$, and $R_7$, which may be identical or different, are chosen from:
hydrogen;
linear or branched $C_1$-$C_4$ alkyl radicals optionally substituted with at least one radical chosen from hydroxyl radicals, $C_1$-$C_2$ alkoxy radicals, carboxamido $CONR_8R_9$ radicals, sulfonyl $SO_2R_8$ radicals and aryl radicals optionally substituted with at least one radical chosen from ($C_1$-$C_4$)alkyl, hydroxyl, $C_1$-$C_2$ alkoxy, amino, and (di)($C_1$-$C_2$)alkylamino radicals; and aryl radicals optionally substituted with at least one radical chosen from ($C_1$-$C_4$)alkyl, hydroxyl, $C_1$-$C_2$ alkoxy, amino, and (di)($C_1$-$C_2$) alkylamino radicals;
$R_6$ and $R_7$, which may be identical or different, may also be chosen from carboxamido radicals $CONR_8R_9$ and sulfonyl radicals $SO_2R_8$;
$R_8$ and $R_9$, which may be identical or different, are chosen from hydrogen; linear or branched $C_1$-$C_4$ alkyl radicals optionally substituted with at least one radical chosen from hydroxyl and $C_1$-$C_2$ alkoxy radicals;
$R_1$ and $R_2$, and $R_3$ and $R_4$, may form, together with the nitrogen atoms to which they are attached, a ring chosen from saturated or unsaturated 5- to 7-membered heterocycles optionally substituted with at least one entity chosen from halogen atoms, amino radicals, (di)($C_1$-$C_4$)alkylamino radicals, hydroxyl radicals, carboxyl radicals, carboxamido radicals, ($C_1$-$C_2$)alkoxy radicals, and $C_1$-$C_4$ alkyl radicals optionally substituted with at least one radical chosen from hydroxyl, amino, (di)alkylamino, alkoxy, carboxyl, and sulfonyl radicals;
$R_3$ and $R_4$ may also form, together with the nitrogen atom to which they are attached, a 5- or 7-membered heterocycle, the carbon atoms of which may be replaced with at least one entity chosen from optionally substituted oxygen and nitrogen atoms;
(b) at least one coupler; and
(c) at least one surfactant chosen from ($C_8$-$C_{30}$)alkyl ether carboxylic acids and salts thereof, ($C_{12}$-$C_{30}$)alkyl polyglucosides, monoglycerolated surfactants, and polyglycerolated surfactants.

30. The method of claim 29, wherein the at least one oxidizing agent is chosen from hydrogen peroxide, urea peroxide, alkali metal bromates, persalts, peracids, and oxidase enzymes.

31. A multi-compartment device comprising at least two compartments, wherein at least one first compartment contains a dye composition and at least one second compartment contains at least one oxidizing agent;
wherein the dye composition comprises, in a suitable medium:
(a) at least one oxidation base chosen from diamino-N,N-dihydropyrazolone derivatives of formula (I) and addition salts thereofs:

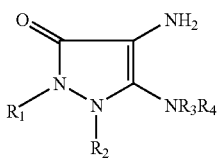

(I)

wherein:
$R_1$, $R_2$, $R_3$, and $R_4$, which may be identical or different, are chosen from:
- linear or branched $C_1$-$C_{10}$ alkyl radicals optionally substituted with at least one radical chosen from $OR_5$ radicals, $NR_6R_7$ radicals, carboxyl radicals, sulfonic radicals, carboxamido radicals $CONR_6R_7$, sulfonamido radicals $SO_2NR_6R_7$, and heteroaryl and aryl radicals optionally substituted with at least one group chosen from $(C_1$-$C_4)$alkyl, hydroxyl, $C_1$-$C_2$ alkoxy, amino, and $(di)(C_1$-$C_2)$alkylamino groups;
- aryl radicals optionally substituted with at least one radical chosen from $(C_1$-$C_4)$alkyl, hydroxyl, $C_1$-$C_2$ alkoxy, amino, and $(di)(C_1$-$C_2)$alkylamino radicals; and
- 5- or 6-membered heteroaryl radicals, optionally substituted with at least one radical chosen from $(C_1$-$C_4)$alkyl and $(C_1$-$C_2)$alkoxy radicals;

$R_3$ and $R_4$ may also be hydrogen atom;

$R_5$, $R_6$, and $R_7$, which may be identical or different, are chosen from:
- hydrogen;
- linear or branched $C_1$-$C_4$ alkyl radicals optionally substituted with at least one radical chosen from hydroxyl radicals, $C_1$-$C_2$ alkoxy radicals, carboxamido $CONR_8R_9$ radicals, sulfonyl $SO_2R_8$ radicals and aryl radicals optionally substituted with at least one radical chosen from $(C_1$-$C_4)$alkyl, hydroxyl, $C_1$-$C_2$ alkoxy, amino, and $(di)(C_1$-$C_2)$alkylamino radicals; and aryl radicals optionally substituted with at least one radical chosen from $(C_1$-$C_4)$alkyl, hydroxyl, $C_1$-$C_2$ alkoxy, amino, and $(di)(C_1$-$C_2)$ alkylamino radicals;

$R_6$ and $R_7$, which may be identical or different, may also be chosen from carboxamido radicals $CONR_8R_9$ and sulfonyl radicals $SO_2R_8$;

$R_8$ and $R_9$, which may be identical or different, are chosen from hydrogen; linear or branched $C_1$-$C_4$ alkyl radicals optionally substituted with at least one radical chosen from hydroxyl and $C_1$-$C_2$ alkoxy radicals;

$R_1$ and $R_2$, and $R_3$ and $R_4$, may form, together with the nitrogen atoms to which they are attached, a ring chosen from saturated or unsaturated 5- to 7-membered heterocycles optionally substituted with at least one entity chosen from halogen atoms, amino radicals, $(di)(C_1$-$C_4)$alkylamino radicals, hydroxyl radicals, carboxyl radicals, carboxamido radicals, $(C_1$-$C_2)$alkoxy radicals, and $C_1$-$C_4$ alkyl radicals optionally substituted with at least one radical chosen from hydroxyl, amino, (di)alkylamino, alkoxy, carboxyl, and sulfonyl radicals;

$R_3$ and $R_4$ may also form, together with the nitrogen atom to which they are attached, a 5- or 7-membered heterocycle, the carbon atoms of which may be replaced with at least one entity chosen from optionally substituted oxygen and nitrogen atoms;

(b) at least one coupler; and (c) at least one surfactant chosen from $(C_8$-$C_{30})$alkyl ether carboxylic acids and salts thereof, $(C_{12}$-$C_{30})$alkyl polyglucosides, monoglycerolated surfactants, and polyglycerolated surfactants.

* * * * *